United States Patent
Hemmi et al.

[11] Patent Number: 5,888,972
[45] Date of Patent: Mar. 30, 1999

[54] PEPTIDE COMPOUNDS, THEIR PREPARATION AND USES

[75] Inventors: Keiji Hemmi, deceased, late of Tsukuba, by Mitsue Hemmi, heir; Masahiro Neya, Tsuchiura; Naoki Fukami, Yuuki-gun; Natsuko Kayakiri, Tsukuba; Hirokazu Tanaka, Takarazuka, all of Japan

[73] Assignee: Fujisawa Pharmaceutical Co., Ltd., Osaka, Japan

[21] Appl. No.: 564,271

[22] PCT Filed: Jun. 28, 1994

[86] PCT No.: PCT/JP94/01042

§ 371 Date: Jun. 24, 1996

§ 102(e) Date: Jun. 24, 1996

[87] PCT Pub. No.: WO95/00537

PCT Pub. Date: Jan. 5, 1995

[30] Foreign Application Priority Data

Jun. 28, 1993 [GB] United Kingdom .................. 9313330

[51] Int. Cl.⁶ .......................... A61K 38/06; A61K 38/07; C07K 5/08

[52] U.S. Cl. .............................. 514/18; 514/19; 530/331; 546/277.4; 546/281.1; 546/284.1; 546/335; 548/495; 549/58; 560/16; 560/41; 562/426; 562/427

[58] Field of Search .................. 530/331; 546/277.4, 546/281.1, 284.1, 335; 548/495; 549/58; 560/16, 41; 562/426, 427, 450; 514/18, 19

[56] References Cited

U.S. PATENT DOCUMENTS

| | | | |
|---|---|---|---|
| 4,921,855 | 5/1990 | Hemmi et al. | 514/235.8 |
| 4,963,530 | 10/1990 | Hemmi et al. | 514/19 |
| 5,223,489 | 6/1993 | Hemmi et al. | 514/19 |
| 5,284,828 | 2/1994 | Hemmi et al. | 514/18 |
| 5,430,022 | 7/1995 | Hemmi et al. | 514/18 |
| 5,491,132 | 2/1996 | Hemmi et al. | 514/18 |

Primary Examiner—Richard L. Raymond

Attorney, Agent, or Firm—Oblon, Spivak, McClelland, Maier & Neustadt, P.C.

[57] ABSTRACT

A compound of the formula:

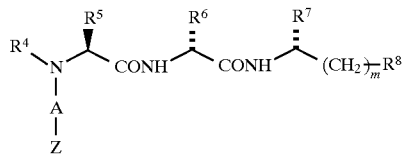

in which $R^4$ is acyl, $R^5$ is lower alkyl, $R^6$ is optionally substituted ar(lower)alkyl or optionally substituted heterocyclic-(lower)alkyl, $R^7$ is lower alkyl or lower alkylthio(lower)alkyl, $R^8$ is carboxy or protected carboxy, A is lower alkylene, Z is a group of the formula:

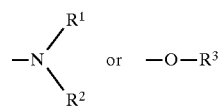

wherein $R^1$ is hydrogen, lower alkyl, common amino-protective group or optionally substituted ar(lower)alkyl, $R^2$ is hydrogen, lower alkyl, optionally substituted ar(lower)alkyl, optionally substituted heterocyclic-(lower)alkyl, optionally substituted cyclo(lower)alkyl (lower)alkyl, common amino-protective group, amino (or protected amino)(lower)alkyl, optionally substituted heterocyclic-carbonyl or cyclo(lower)alkyl, and $R^3$ is optionally substituted heterocyclic(lower)alkyl, and m is an integer of 0 to 2, or pharmaceutically acceptable salts thereof, useful as endothelin antagonist.

9 Claims, No Drawings

PEPTIDE COMPOUNDS, THEIR PREPARATION AND USES

This application is a 371 of PCT/JP94/01042, filed Jun. 28, 1994.

TECHNICAL FIELD

The present invention relates to new compound and a pharmaceutically acceptable salt thereof.

More particularly, it relates to new peptide compound and a pharmaceutically acceptable salt thereof which have pharmacological activities such as endothelin antagonistic activity and the like, to processes for its preparation, to a pharmaceutical composition comprising the same, and to a method of using the same therapeutically in the treatment and the prevention of endothelin mediated diseases such as hypertension, and the like.

Pharmacological and structural evidence supports the existence of at least two endothelin receptor subtypes, i.e., $ET_A$ and $ET_B$. $ET_A$ receptors are distributed predominantly in vascular smooth muscle, heart and intestine, whereas $ET_B$ receptors are found in cerebral cortex, lung and kidney. Recently, it is found that in addition to $ET_A$ receptors, vasoconstrictor $ET_B$ receptors are also present on vascular smooth muscle. $ET_A$ receptors have a higher affinity to ET-1 than ET-3 and sarafotoxin S6c, while $ET_B$ receptors show nearly the same affinity to all isoforms of ET and sarafotoxin peptides.

The compounds of this invention may have $ET_B$ antagonistic activity.

One object of the present invention is to provide new and useful peptide compound and a pharmaceutically acceptable salt thereof which have pharmacological activities such as endothelin, particularly $ET_B$ antagonistic activity and the like.

Another object of the present invention is to provide processes for the preparation of said peptide compound and a salt thereof.

A further object of the present invention is to provide a pharmaceutical composition comprising, as an active ingredient, said peptide compound or a pharmaceutically acceptable salt thereof.

Still further object of the present invention is to provide a method of using the same for the treatment and the prevention of endothelin, particularly $ET_B$ mediated diseases such as hypertension, and the like.

DISCLOSURE OF INVENTION

The object compound of the present invention can be represented by the following general formula (I).

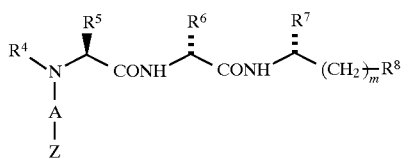

in which
R$^4$ is acyl,
R$^5$ is lower alkyl,
R$^6$ is optionally substituted ar(lower)alkyl or optionally substituted heterocyclic-(lower)alkyl,
R$^7$ is lower alkyl or lower alkylthio(lower)alkyl,
R$^8$ is carboxy or protected carboxy,
A is lower alkylene,
Z is a group of the formula:

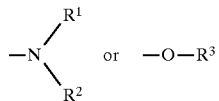

wherein
R$^1$ is hydrogen, lower alkyl, common amino-protective group or optional substituted ar(lower)alkyl,
R$^2$ is hydrogen, lower alkyl, optionally substituted ar(lower)alkyl, optionally substituted heterocyclic-(lower)alkyl, optionally substituted cyclo(lower)alkyl (lower)alkyl, common amino-protective group, amino (or protected amino)(lower)alkyl, optionally substituted heterocyclic-carbonyl or cyclo(lower)alkyl,
R$^3$ is optionally substituted heterocyclic(lower)alkyl, and
m is an integer of 0 to 2,
or pharmaceutically acceptable salts thereof.

According to the present invention, the new peptide compound (I) and a salt thereof can be prepared by the processes as shown in the following schemes.

Process 1

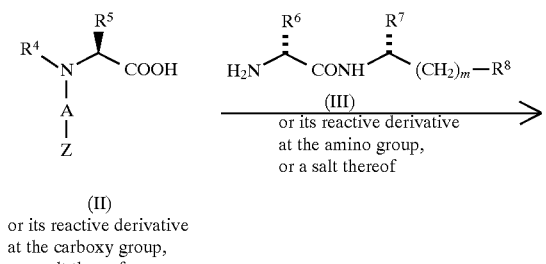

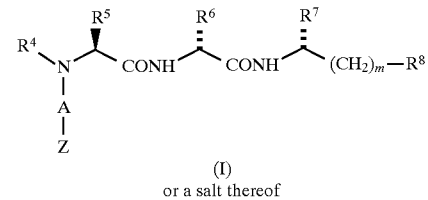

Process 2

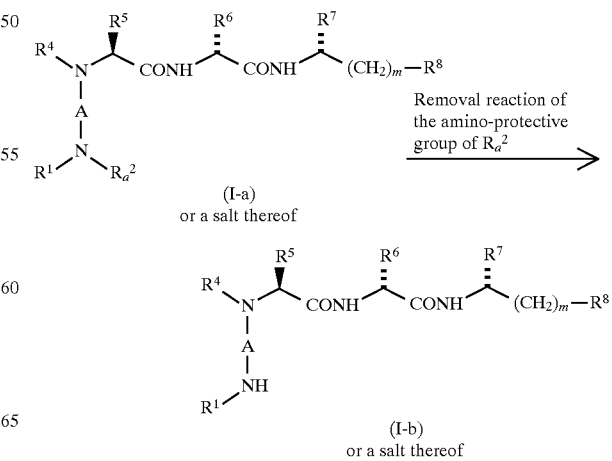

Process 3

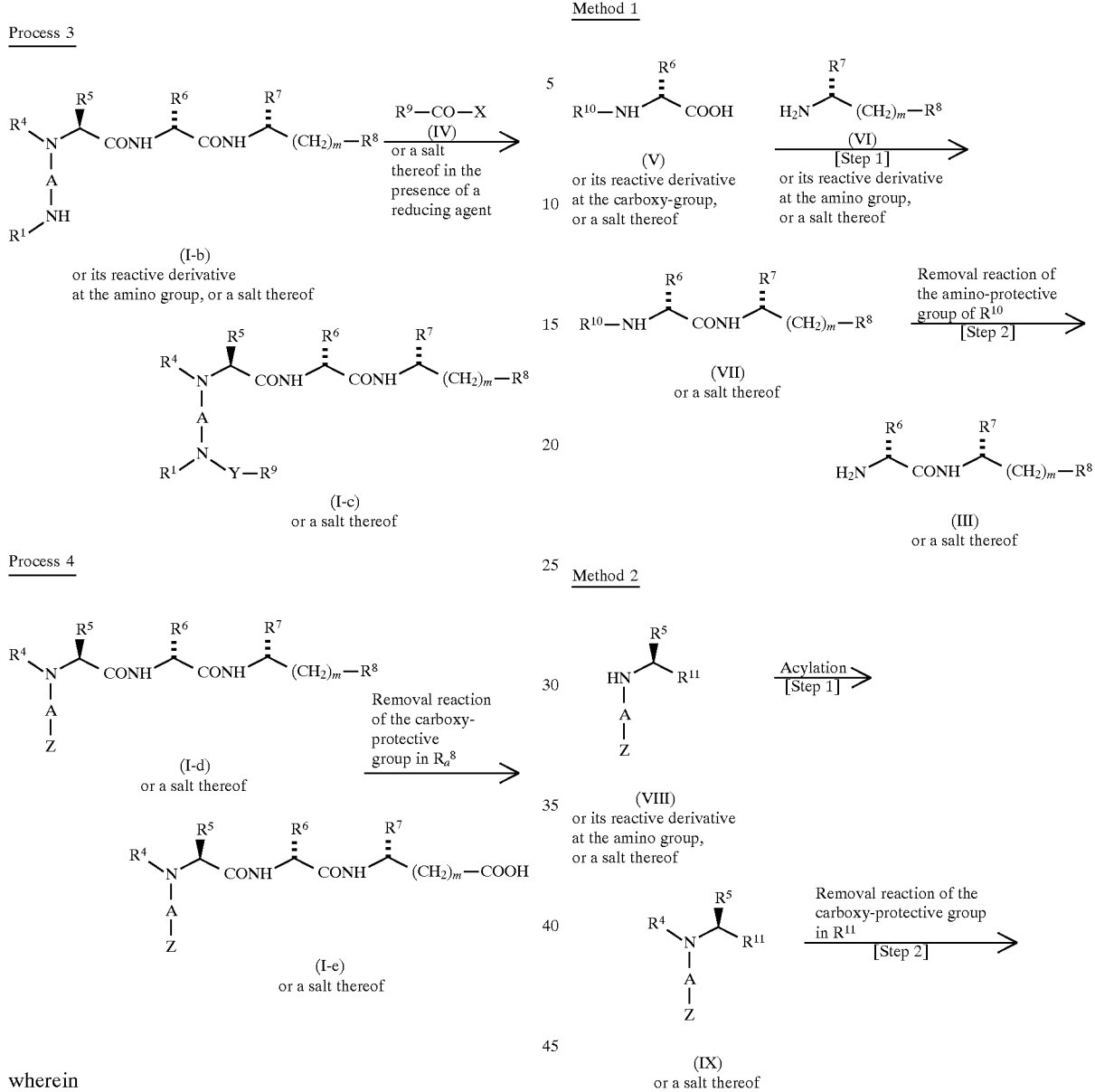

Process 4 wherein $R^1$, $R^2$, $R^3$, $R^4$, $R^5$, $R^6$, $R^7$, $R^8$, A, Z and m are each as defined above, $R_a^2$ is amino-protective group, $R_a^8$ is protected carboxy, $R^9$ is hydrogen, $C_1$–$C_5$ alkyl, optionally substituted ar($C_1$–$C_5$)alkyl, optionally substituted heterocyclic ($C_1$–$C_5$)alkyl, optionally substituted cyclo(lower)alkyl ($C_1$–$C_5$)alkyl, or amino(or protected amino)($C_1$–$C_5$)alkyl, X is a leaving group or hydrogen, and Y is methylene or carbonyl.

Some of the starting compounds used in the above Processes are novel and can be prepared according to the following Methods and/or by the procedures described in the following Preparations or by a conventional manner.

Method 2

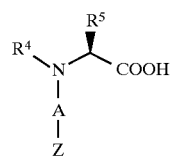

wherein
$R^4$, $R^5$, $R^6$, $R^7$, $R^8$, A, Z and m are each as defined above,
$R^{10}$ is amino-protective group, and
$R^{11}$ is protected carboxy.

Suitable pharmaceutically acceptable salts of the object compound (I) may be a conventional non-toxic salt and include an acid addition salt such as an organic acid salt (e.g. acetate, trifluoroacetate, maleate, tartrate, fumarate, methanesulfonate, benzenesulfonate, formate, toluenesulfonate, etc.), an inorganic acid salt (e.g.

hydrochloride, hydrobromide, hydriodide, sulfate, nitrate, phosphate, etc.), or a salt with a base such as an amino acid (e.g. arginine, aspartic acid, glutamic acid, etc.), an alkali metal salt (e.g. sodium salt, potassium salt, etc.), an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention includes within the scope thereof are explained in detail as follows.

Throughout the present specification, the amino acids, peptides, protective groups, condensing agents, etc. are indicated by the abbreviations according to the IUPAC-IUB (Commission on Biological Nomenclature) which are in common use in a field of this art.

The term "lower" is intended to mean 1 to 6, preferably 1 to 4 carbon atoms, and the term "higher" is intended to mean more than 6, preferably 7 to 12 carbon atoms, unless otherwise indicated.

Suitable "acyl" may include an aliphatic acyl, an aromatic acyl, a heterocyclic acyl and an aliphatic acyl substituted with aromatic or heterocyclic group(s) derived from acids such as carboxylic, carbonic, carbamic, sulfonic acids.

The aliphatic acyl may include saturated or unsaturated, acyclic or cyclic ones, such as carbamoyl, lower alkanoyl (e.g. formyl, acetyl, propionyl, butyryl, isobutyryl, 3,3-dimethylbutyryl, 4,4-dimethylvaleryl, valeryl, isovaleryl, pivaloyl, hexanoyl, 3-methylvaleryl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, t-butoxycarbonyl, etc.), lower alkenoyl (e.g. acryloyl, methacryloyl, crotonoyl, etc.), ($C_3$–$C_7$)cycloalkanecarbonyl (e.g. cyclohexanecarbonyl, etc.), ($C_3$–$C_7$)cycloalkyl(lower)alkanoyl (e.g. cyclohexylacetyl, etc.), amidino, protected carboxycarbonyl such as lower alkoxalyl (e.g. methoxalyl, ethoxalyl, t-butoxalyl, etc.), $C_3$–$C_7$ cycloalkyloxycarbonyl (e.g. cyclohexyloxycarbonyl, etc.), (heterocyclic acyl)(lower)alkanoyl, wherein said heterocyclic acyl being the same as those mentioned below, such as morpholinocarbonyl(lower)alkanoyl (e.g. 3-morpholinocarbonylpropanoyl, etc.), lower or higher alkylcarbamoyl (e.g. methylcarbamoyl, ethylcarbamoyl, propylcarboamoyl, isopropylcarbamoyl, butylcarbamoyl, 2-methylbutylcarbamoyl, pentylcarbamoyl, 1,3-dimethylbutylcarbamoyl, hexylcarbamoyl, hepthylcarbamoyl, octylcarbamoyl, nonylcarbamoyl, etc.), di(lower)alkylcarbamoyl (e.g. N-methyl-N-ethylcarbamoyl, dimethylcarbamoyl, diethylcarbamoyl, dipropylcarbamoyl, diisopropylcarbamoyl, dibutylcarbamoyl, diisobutylcarbamoyl, dihexylcarbamoyl, etc.), $C_3$–$C_7$ cycloalkylcarbamoyl (e.g. cyclopropylcarbamoyl, cyclobutylcarbamoyl, cyclopentylcarbamoyl, cyclohexylcarbamoyl, cycloheptylcarbamoyl, etc.), N-lower alkyl-N-($C_3$–$C_7$)cycloalkylcarbamoyl (e.g. N-methyl-N-cyclopropylcarbamoyl, N-methyl-N-cyclohexylcarbamoyl, N-ethyl-N-cyclohexylcarbamoyl, N-propyl-N-hexylcarbamoyl, etc.), di($C_3$–$C_7$)cyclohexylcarbamoyl (e.g. dicyclopropylcarbamoyl, dicyclopentylcarbamoyl, dicyclohexylcarbamoyl, etc.), N-[di(lower)alkylcarbamoyl ($C_3$–$C_7$)cycloalkyl]carbamoyl [e.g. N-(1-(or 4-)dimethylcarbamoylcyclohexyl)carbamoyl, etc.], N-[di(lower)alkylcarbamoyl(lower)alkyl($C_3$–$C_7$)cycloalkyl] carbamoyl [e.g. N-[1-(or 4-)(dimethylcarbamoylmethyl) cyclohexyl]carbamoyl, etc.], N-[carbamoyl(lower)alkyl] carbamoyl [e.g. N-[1-carbamoyl-2-methylbutyl]carbamoyl, etc.], N-[N-(lower)alkylcarbamoyl(lower)alkyl]carbamoyl [e.g. N-(1-isopropylcarbamoyl-2-methylbutyl)carbamoyl, etc.], N-[N,N-lower alkylenecarbamoyl(lower)alkyl] carbamoyl [e.g. N-[2-methyl-1-(piperidinocarbamonyl) butyl]carbamoyl, etc.], N-[N,N-di(lower)alkylcarbamoyl (lower)alkyl]carbamoyl [e.g. N-(dimethylcarbamoylmethyl) carbamoyl, N-[1-(or 2-)(dimethylcarbamoyl)ethyl] carbamoyl, N-[1-(dimethylcarbamoyl)-2-methylpropyl] carbamoyl, N-[2,2-dimethyl-1-(dimethylcarbamoyl)propyl] carbamoyl, N-[2-methyl-1-(dimethylcarbamoyl)butyl] carbamoyl, N-[2-methyl-1-(diethylcarbamoyl)butyl] carbamoyl, N-[3-methyl-1-(dimethylcarbamoyl)butyl] carbamoyl, N-(1-dimethylcarbamoylpentyl)carbamoyl, etc.], N-(lower)alkyl-N-[N,N-di(lower)alkylcarbamoyl] (lower)alkylcarbamoyl [e.g. N-methyl-N-[1-dimethylcarbamoyl-2-methylbutyl]carbamoyl, N-methyl-N-[1-dimethylcarbamoyl-3-methylbutyl]carbamoyl, etc.], N-[N-(lower)cycloalkylcarbamoyl(lower)alkyl]carbamoyl [e.g. N-(1-cyclohexylcarbamoyl-2-methylbutyl)carbamoyl, etc.], and the like.

The aromatic acyl may include ($C_6$–$C_{10}$)aroyl (e.g. benzoyl, toluoyl, xyloyl, naphtoyl, etc.), ($C_6$–$C_{10}$) arenesulfonyl (e.g. benzenesulfonyl, tosyl, etc.), ($C_6$–$C_{10}$) arylcarbamoyl (e.g. phenylcarbamoyl, tolylcarbamoyl, etc.), ($C_6$–$C_{10}$)aryloxalyl (e.g. phenyloxalyl, etc.), and the like.

The heterocyclic acyl, wherein said heterocyclic group may be the same as mentioned below, may include heterocyclecarbonyl (e.g. furoyl, thenoyl, 2-(or 3- or 4-)pyridylcarbonyl, thiazolylcarbonyl, thiadiazolylcarbonyl, tetrazolylcarbonyl, piperazinylcarbonyl, morpholinocarbonyl, thiomorpholinocarbonyl, indolylcarbonyl, etc.), lower or higher alkyleneaminocarbonyl (e.g. aziridin-1-ylcarbonyl, azetidin-1-ylcarbonyl, pyrrolidin-1-ylcarbonyl, piperidin-1-ylcarbonyl, hexahydro-1H-azepin-1-ylcarbonyl, octahydroazocin-1-ylcarbonyl, tetrahydroquinolinecarbonyl, tetrahydroisoquinolinecarbonyl, dihydropyridinecarbonyl, tetrahydropyridinecarbonyl, etc.), heterocyclic-carbamoyl wherein said heterocyclic group may be the same as mentioned below (e.g. pyridylcarbamoyl, piperidylcarbamoyl, hexahydro-1H-azepinylcarbamoyl, etc.), and the like.

The aliphatic acyl substituted with aromatic group(s) may include ($C_6$–$C_{10}$)ar(lower)alkanoyl such as phenyl(lower) alkanoyl (e.g. phenylacetyl, phenylpropionyl, phenylhexanoyl, naphthylacetyl etc.), ($C_6$–$C_{10}$)ar(lower) alkoxycarbonyl such as phenyl(lower)alkoxycarbonyl (e.g. benzyloxycarbonyl, phenethyloxycarbonyl, etc.), phenoxy (lower)alkanoyl (e.g. phenoxyacetyl, phenoxypropionyl, etc.), ($C_6$–$C_{10}$)ar(lower)alkoxalyl such as phenyl(lower) alkoxalyl (e.g. benzyloxalyl etc.), ($C_6$–$C_{10}$)ar(lower) alkenoyl such as phenyl(lower)alkenoyl (e.g. cinnamoyl, etc.), ($C_6$–$C_{10}$)ar(lower)alkylsulfonyl (e.g. benzylsulfonyl, etc.), and the like.

The aliphatic acyl substituted with heterocyclic group(s) may include heterocyclic-(lower)alkanoyl, wherein said heterocyclic group may be the same as mentioned below (e.g. thienylacetyl, imidazolylacetyl, furylacetyl, tetrazolylacetyl, thiazolylacetyl, thiadiazolylacetyl, thienylpropionyl, thiadiazolylpropionyl, pyridylacetyl, etc.), heterocyclic-(lower)alkylcarbamoyl, wherein said heterocyclic group may be the same as mentioned below (e.g. pyridylmethylcarbamoyl, morpholinoethylcarbamoyl, etc.), and the like.

These acyl groups may be further substituted with one or more, preferably one to three suitable substituent(s) such as hydroxy, lower alkyl (e.g. methyl, ethyl, propyl, isopropyl, butyl, t-butyl, pentyl, hexyl, etc.), halogen (e.g. chlorine, bromine, iodine, fluorine), carbamoyl, oxo, di(lower) alkylcarbamoyl, amino, protected amino such as lower alkanoylamino (e.g. formamido, acetamido, propionamido, etc.), (lower)alkoxycarbonylamino (e.g. t-butoxycarbonylamino, etc.), lower alkylsulfonyl (e.g. methylsulfonyl, etc.), arylsulfonyl (e.g. phenylsulfonyl, tosyl, etc.), ar(lower)alkyl (e.g. benzyl, etc.), lower alkoxy (e.g. methoxy, ethoxy, propoxy, isopropoxy, butoxy, t-butoxy, etc.), carboxy, protected carboxy as mentioned below, carboxy(lower)alkyl (e.g. carboxymethyl, carboxyethyl, etc.), protected carboxy(lower)alkyl (e.g. t-butoxycarbonylmethyl, etc.) and the like.

Suitable examples of the above acyl groups which is further substituted with one or more, preferably one to three suitable substituent(s) may be halophenyl(lower)alkanoyl (e.g., 2-chlorophenylacetyl, etc.), (aminophenyl)(lower) alkanoyl (e.g. 4-aminophenylacetyl, etc.), [(lower alkoxycarbonylamino)phenyl](lower)alkanoyl [e.g. 4-(t-butoxycarbonylamino)phenylacetyl, etc.], amino(lower) alkanoyl (e.g. 2-amino-3-methylpentanoyl, etc.), (lower alkoxycarbonylamino)(lower)alkanoyl [e.g. 2-(t-butoxycarbonylamino)-3-methylpentanoyl, etc.), lower alkanoyl substituted by suitable substituent(s) such as phenyl, amino, lower alkoxycarbonyl amino, etc. [e.g. 2-amino-2-phenylacetyl, 2-(t-butoxycarbonylamino)-2-phenylacetyl, etc.], di(lower)alkylpiperidinylcarbonyl [e.g. 2,6-(or 3,5-)dimethylpyperidin-1-ylcarbonyl, etc.], [di (lower)alkylcarbamoyl]piperidinylcarbonyl [e.g. 4-(dimethylcarbamoyl)piperidin-1-ylcarbonyl, etc.], [di (lower)alkylcarbamoyl]pyrrolidinylcarbonyl [e.g. 2-(dimethylcarbamoyl)pyrrolidin-1-ylcarbonyl, etc.], piperazinylcarbonyl substituted by suitable substituent(s) such as lower alkyl, oxo, etc. [e.g. 4-methyl-3-oxo-2-(1-methylpropyl)piperazin-1-ylcarbonyl, etc.], N-(lower)alkyl-N-[hydroxy(lower)alkyl]carbamoyl [e.g. N-methyl-N-(2-hydroxyethyl)carbamoyl, etc.], N-[hydroxy(lower)alkyl] carbamoyl [e.g. N-{1-(hydroxymethyl)-3-methylbutyl}carbamoyl, etc.], N-[(C$_3$–C$_7$)cycloalkyl(lower) alkyl]carbamoyl [e.g. N-(cyclohexylmethyl)carbamoyl, etc.], N-[carboxy(lower)alkyl]carbamoyl [e.g. N-(1-carboxy-2-methylbutyl)carbamoyl, etc.], N-[(lower) alkoxycarbonyl(lower)alkyl]carbamoyl [e.g. N-(1-methoxycarbonyl-2-methylbutyl)carbamoyl, etc.], (oxoheterocyclic)carbamoyl wherein said heterocyclic group may be the same as mentioned below such as {oxo (hexahydro-1H-azepinyl)}carbamoyl (e.g. ε-caprolactam-3-yl, etc.), etc., N-[N-(lower)alkoxycarbonylpiperidinyl] carbamoyl [e.g. N-(N-ethoxycarbonylpiperidin-4-yl) carbamoyl, etc.], N-[N,N-di(lower)alkylcarbamoyl(lower) alkyl]carbamoyl substituted by phenyl or cyclo(lower)alkyl [e.g. N-{1-(N,N-dimethylcarbamoyl)-1-phenylmethyl}carbamoyl, N-{1-(N,N-dimethylcarbamoyl)-1-cyclohexylmethyl}carbamoyl, etc.], N-[hydroxy(C$_3$–C$_7$) cycloalkyl]carbamoyl [e.g. N-(4-hydroxycyclohexyl) carbamoyl, etc.], N-(lower)alkoxyphenylcarbamoyl [e.g. N-(4-methoxyphenyl)carbamoyl, etc.], N-(lower alkanoylamino)carbamoyl [e.g. N-(2-methylpropanoylamino)carbamoyl, etc.], and the like.

Preferable example of the acyl group may be (C$_6$–C$_{10}$)ar (lower)alkanoyl optionally substituted by halogen such as phenyl(lower)alkanoyl, halophenyl(lower)alkanoyl, and the like, C$_6$–C$_{10}$ arylcarbamoyl optionally substituted by halogen such as phenylcarbamoyl, halophenylcarbamoyl, in which most preferable one may be phenylacetyl, 2-chlorophenylacetyl, phenylcarbamoyl and 2-chlorophenylcarbamoyl.

Suitable "lower alkyl" may include a straight or branched one such as methyl, ethyl, propyl, isopropyl, butyl, isobutyl, tert-butyl, pentyl, hexyl, and the like, in which the most preferred example may be methyl and butyl for $R^1$ and/or $R^2$ isobutyl for $R^5$, and isopropyl and isobutyl for $R^7$.

Suitable "protected carboxy" may include esterified carboxy and amidated carboxy as mentioned above.

"Esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s) for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], aroyl(lower)alkyl ester such as benzoyl(lower)alkyl ester (e.g. phenacyl ester, etc.), lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], phthalidyldene (lower)alkyl ester, or (5-lower alkyl-2-oxo-1,3-dioxol-4-yl) (lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis (methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

Preferable examples of the esterified carboxy thus defined may be lower alkoxycarbonyl, and the most preferable one may be methoxycarbonyl and ethoxycarbonyl for $R^8$, and ethoxycarbonyl for $R^{11}$.

Suitable "optionally substituted heterocyclic-(lower) alkyl" means aforementioned lower alkyl, which is substituted by saturated or unsaturated, monocyclic or polycyclic heterocyclic group containing at least one hetero-atom such as an oxygen sulfur, nitrogen atom and the like.

More preferable heterocyclic moiety may be heterocyclic group such as:

unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1, 2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

saturated 3 to 8-membered, preferably 5 or 6-membered heteromonocyclic group containing 1 to 4 nitrogen atom(s), for example, azetidinyl, pyrrolidinyl, imidazolidinyl, piperidinyl, pyrazolidinyl, piperazinyl, etc.;

unsaturated condensed 7 to 12-membered heterocyclic group containing 1 to 5 nitrogen atom(s), for example, indolyl, isoindolyl, indolizinyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.;

unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.;

saturated 3 to 8-membered, preferably 5 or 6-membered heteromonocyclic group containing 1 to 2 oxygen atom(s) and 1 to 3 nitrogen atom(s), for example, morpholinyl, etc.;

unsaturated condensed 7 to 12-membered heterocyclic group containing 1 to 2 oxygen atom(s) and 1 to 3 nitrogen atom(s), for example, benzoxazolyl, benzoxadiazolyl, etc.;

unsaturated 3 to 8-membered, preferably 5 or 6-membered heteromonocyclic group containing 1 to 2 sulfur atom(s) and 1 to 3 nitrogen atom(s), for example, thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl, etc.), etc.;

saturated 3 to 8-membered, preferably 5 or 6-membered heteromonocyclic group containing 1 to 2 sulfur atom (s) and 1 to 3 nitrogen atom(s), for example, thiazolidinyl, etc.;

unsaturated 3 to 8-membered, preferably 5 or 6-membered heteromonocyclic group containing a sulfur atom, for example, thienyl, etc.;

unsaturated condensed 7 to 12-membered heterocyclic group containing 1 to 3 sulfur atom(s), for example, benzothienyl (e.g. benzo[b]thienyl, etc.), unsaturated condensed 7 to 12-membered heterocyclic group containing 1 to 2 sulfur atom(s) and 1 to 3 nitrogen atom(s), for example, benzothiazolyl, benzothiadiazolyl, etc. and the like;

wherein said heterocyclic group may be substituted by one or more, preferably one or two suitable substituent (s) such as:

hydroxy;

protected hydroxy, in which the hydroxy group is protected by a conventional hydroxy-protective group such as acyl as mentioned above, tri(lower) alkylsilyloxy (e.g. t-butyldimethylsilyloxy, etc.), etc.;

halogen (e.g. chlorine, bromine, iodine or fluorine);

lower alkoxy, which may be straight or branched one such as methoxy, ethoxy, propoxy, isopropoxy, butoxy, pentyloxy, hexyloxy, etc., more preferably $C_1$–$C_4$ alkoxy (e.g. methoxy, etc.);

lower alkyl as mentioned above, more preferably $C_1$–$C_4$ alkyl (e.g. methyl, etc.); amino, nitro; cyano; and the like.

And further when said heterocyclic group has imino-moiety(ies) in its ring, the imino-moiety(ies) may be substituted by suitable substituent(s) such as;

lower alkyl as mentioned above (e.g. methyl, ethyl, propyl, isobutyl, etc.);

imino-protective group, same as amino-protective group as mentioned below, more preferably lower alkanoyloxycarbonyl (e.g. formyl, etc.), arenesulfonyl (e.g. tosyl, etc.); and the like.

Preferable example of "optionally substituted heterocyclic-(lower)alkyl" thus defined may be lower alkyl substituted by unsaturated 5 or 6-membered heteromonocyclic group containing 1 to 4 nitrogen atom(s), such as pyridyl(lower)alkyl; imidazolyl(lower)alkyl; lower alkyl substituted by unsaturated concensed 7 to 12-membered heterocyclic group containing 1 to 5 nitrogen atom(s), optionally substituted by lower alkyl, such as indolyl, lower alkylindolyl; lower alkyl substituted by unsaturated condensed 7 to 12-membered heterocyclic group containing 1 to 3 sulfur atom(s), such as benzothienyl; and the most preferable one may be 3-pyridylmethyl for $R^2$ and $R^3$, and 1-methylindol-3-yl and 3-benzo[b]thienyl for $R^6$.

Suitable "ar(lower)alkyl" moiety may include $C_6$–$C_{10}$ar (lower)alkyl such as phenyl(lower)alkyl (e.g. benzyl, phenethyl, etc.), tolyl(lower)alkyl, xylyl(lower)alkyl, naphthyl(lower)alkyl (e.g. naphthylmethyl, etc.), and the like, wherein said ar(lower)alkyl may be substituted by suitable substituent(s) such as those mentioned in the explanation of "optionally substituted heterocyclic-(lower)alkyl" as mentioned above.

Preferable example of "optionally substituted ar(lower) alkyl" thus defined may be phenyl(lower)alkyl optionally substituted by halogen, lower alkyl or lower alkoxy, and naphthyl(lower)alkyl, and the most preferable one may be benzyl optionally substituted by chloro, methyl or methoxy, and naphthylmethyl for $R^1$ and/or $R^2$, and naphthylmethyl for $R^6$.

Suitable "optionally substituted cyclo(lower)alkyl(lower) alkyl" means aforementioned lower alkyl which is substituted by $C_3$–$C_7$ cyclo(lower)alkyl such as cyclopropyl, cyclobutyl, cyclopentyl, cyclohexyl, cycloheptyl, and the like, wherein said cyclo(lower)alkyl(lower)alkyl is optionally substituted by suitable substituent(s) such as those mentioned in the explanation of "optionally substituted heterocyclic(lower)alkyl" as mentioned before, in which more preferable example may be $C_4$–$C_6$ cyclo(lower)alkyl and the most preferable one may be cyclohexylmethyl.

Suitable "lower alkylene" means straight or branched one such as methylene, ethylene, trimethylene, methylethylene, tetramethylene, pentamethylene, hexamethylene, and the like, in which most preferable example may be ethylene, trimethylene and propylene.

Suitable "lower alkylthio(lower)alkyl" means straight or branched lower alkyl substituted by lower alkylthio such as methylthio, ethylthio, propylthio, isopropylthio, butylthio, pentylthio, hexylthio, and the like, in which more preferable example may be $C_1$–$C_4$ alkylthio($C_1$–$C_4$)alkyl and the most preferable one may be methylthiomethyl.

Suitable "amino(or protected amino)(lower)alkyl" means aforementioned lower alkyl substituted by amino or protected amino group, wherein said protected amino group is protected by common amino-protective group as mentioned below, in which more preferable example may be amino (lower)alkyl, lower alkoxycarbonylamino(lower)alkyl and $C_6$–$C_{10}$ aryl(lower)alkylamino(lower)alkyl, and the most preferable one may be 2-aminopropyl and 2-(tert-butoxycarbonylamino)propyl.

Suitable "optionally substituted heterocyclic-carbonyl" means carbonyl group substituted by heterocyclic group as mentioned above, in which more preferable example may be carbonyl group substituted by unsaturated 5 or 6-membered heteromonocyclic group containing 1 to 4 nitrogen atom(s), and the most preferable one may be pyridylcarbonyl.

Suitable "cyclo(lower)alkyl" may include $C_3$–$C_6$ cyclo(lower)alkyl such as cyclopropyl, cyclobutyl, cyclopentyl, cyclohexyl, and the like, in which most preferable example may be cyclohexyl.

Suitable "leaving group" may include acid residue such as halogen (e.g. fluoro, chloro, bromo, iodo), acyloxy (e.g. acetoxy, tosyloxy, mesyloxy, etc.), and the like, in which more preferable example may be chloro.

Suitable "common amino-protective group" may include acyl as mentioned above, ar(lower)alkyl as mentioned above, in which more preferable example may be lower alkoxycarbonyl and phenyl(lower)alkyl, and the most preferable one may be t-butoxycarbonyl and benzyl.

Suitable "$C_1$–$C_5$ alkyl", "optionally substituted ar($C_1$–$C_5$)alkyl", "optionally substituted heterocyclic($C_1$–$C_5$)alkyl", "optionally substituted cyclo(lower)alkyl($C_1$–$C_5$)alkyl" and "amino(or protected amino)($C_1$–$C_5$)alkyl", respectively means aforementioned lower alkyl, optionally substituted ar(lower)alkyl, optionally substituted heterocyclic-(lower)alkyl, optionally substituted cyclo(lower)alkyl(lower)alkyl and amino(or protected amino)(lower)alkyl, wherein said lower alkyl moieties have $C_1$–$C_5$ carbon atoms.

One preferred embodiments of each definition of the compound (I) may be as follows.

$R^1$ is hydrogen, lower alkyl, phenyl(lower)alkyl optionally substituted by the group consisting of halogen, lower alkyl and lower alkoxy, or naphthyl(lower)alkyl, $R^2$ is hydrogen, lower alkyl, phenyl(lower)alkyl optionally substituted by the group consisting of halogen, lower alkyl and lower alkoxy, aphthyl(lower)alkyl, pyridyl(lower)alkyl, cyclo(loer)alkyl(lower)alkyl, or amino-protective group such as lower alkoxycarbonyl, $R^3$ is pyridyl(lower)alkyl, $R^4$ is ar(lower)alkanoyl optionally substituted by halogen, $R^5$ is lower alkyl (e.g. isobutyl), $R^6$ is naphthyl(lower)alkyl, $R^7$ is lower alkyl (e.g. isopropyl), $R^8$ is carboxy or protected carboxy such as lower alkoxycarbonyl, and m is an integer of 0.

Another preferred embodiments of each definition of the compound (I) may be as follows.

$R^1$ is hydrogen, lower alkyl, lower alkoxycarbonyl, phenyl(lower)alkyl optionally substituted by the group consisting of halogen, lower alkyl and lower alkoxy, or naphthyl(lower)alkyl, $R^2$ is hydrogen, lower alkyl, phenyl(lower)alkyl optionally substituted by the group consisting of halogen, lower alkyl and lower alkoxy, naphthyl(lower)alkyl, pyridyl(lower)alkyl, cyclo(lower)alkyl(lower)alkyl, amino(or lower alkoxycarbonylamino)(lower)alkyl, cyclo(lower)alkyl, pyridylcarbonyl, or lower alkoxycarbonyl, $R^3$ is pyridyl(lower)alkyl, $R^4$ is $C_6$–$C_{10}$ ar(lower)alkanoyl optionally substituted by halogen, or $C_6$–$C_{10}$ arylcarbamoyl optionally substituted by halogen, $R^5$ is lower alkyl, $R^6$ is naphthyl(lower)alkyl, lower alkylindolyl(lower)alkyl, benzothienyl(lower)alkyl, $R^7$ is lower alkyl or lower alkylthio(lower)alkyl, $R^8$ is carboxy or lower alkoxycarbonyl, and m is an integer of 0.

Further, more preferred embodiment of the compound (I) can be represented by the following formula:

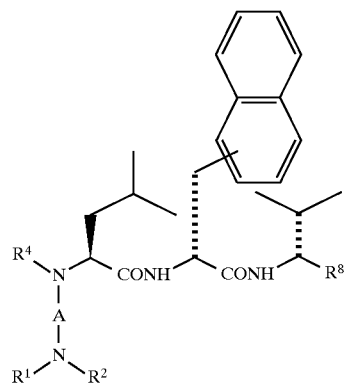

in which $R^1$, $R^2$, $R^4$, $R^8$ and A are each as defined above.

The processes for preparing the object compound (I) are explained in detail in the following.

Process 1

The object compound (I) or a salt thereof can be prepared by reacting the compound (II) or its reactive derivative at the carboxy group, or a salt thereof with the compound (III) or its reactive derivative at the amino group, or a salt thereof.

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by reaction of the compound (III) with phosphorus trichloride or phosgene, and the like.

Suitable salts of the compound (III) and its reactive derivative can be referred to the acid addition salts as exemplified for the compound (I).

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminiomethyl

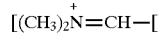

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

Suitable salts of the compound (II) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt N,N'-dibenzylethylenediamine salt, etc.], or the like.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxasolium salt; 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)-alkylmorpholine, N,N-di(lower)alkylbenzylamine, or the like.

The reaction temperature is not critical, and the reaction is usually carried out under cooling to warming.
Process 2

The object compound (I-b) or a salt thereof can be prepared by subjecting a compound (I-a) or a salt thereof to a removal reaction of the amino-protective group of $R_a^2$.

Suitable salts of the compounds (I-a) and (I-b) can be referred to the ones as exemplified for the compound (I).

This reaction is carried out in accordance with a conventional method such as solvolysis including hydrolysis, reduction or the like.

The solvolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.].

The removal reaction using Lewis acid such as trihaloacetic acid [e.g. trichloroacetic acid, trifluoroacetic acid, etc.] or the like, is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, carbon tetrachloride, tetrahydrofuran, N,N-dimethylformamide, a mixture thereof or any other solvent which does not adversely influence the reaction. A liquid base or acid can be also used as the solvent. The reaction temperature is not critical and the reaction is usually carried out under cooling to heating.

The reduction method applicable for the removal reaction may include chemical reduction and catalytic reduction.

Suitable reducing agents to be used in chemical reduction are, chemical reducing agent such as lithium aluminum hydride, sodium borohydride, sodium cyanoborohydride, etc., a combination of metal [e.g. tin, zing, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], and the like.

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acid to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.
Process 3

The object compound (I-c) or a salt thereof can be prepared by reacting the compound (I-b) or its reactive derivative at the amino group, or a salt thereof with the compound (IV), or a salt thereof in the presence of a suitable reducing agent.

Suitable reactive derivative of the compound (I-b) can be referred to the ones as exemplified for the compound (III).

Suitable salts of the compound (I-c) can be referred to the ones as exemplified for the compound (I).

Suitable reducing agent can be referred to the ones exemplified for the Process 2, wherein said reducing agent can reduce the imino function intermediately prepared such as sodium borohydride, sodium cyanoborohydride, catalytic reducing agent, and the like.

This reaction can be carried out in substantially the same manner as Processes 1 and/or 2, and therefore the reaction mode and reaction conditions [e.g. reactive derivatives, solvents, reaction temperature, etc.] of this reaction are to be referred to those as explained in Processes 1 and 2.

Process 4

The object compound (I-e) or a salt thereof can be prepared by subjecting a compound (I-d) or a salt thereof to a removal reaction of the carboxy-protective group in $R_a^8$.

Suitable salts of the compound (I-d) and (I-e) can be referred to ones as exemplified for the compound (I).

This removal reaction can be carried out by a conventional method in the peptide chemistry such as solvolysis, reduction, and the like, the details of which can be referred to those of Process 2.

The compounds obtained by the above processes can be isolated and purified by a conventional method such as pulverization, recrystallization, column chromatography, reprecipitation, or the like.

The object compound (I) can be transformed into its salt in a conventional manner.

The method for preparing the new starting compounds are explained in detail in the following.

Method 1

[Step 1]

The compound (VII) or a salt thereof can be prepared by reacting the compound (V) or its reactive derivative at the carboxy group, or a salt thereof with the compound (VI) or its reactive derivative at the amino group, or a salt thereof.

Suitable salts of the compound (V) and its reactive derivative can be referred to the ones as exemplified for the compound (II).

Suitable salts of the compound (VI) and its reactive derivative can be referred to the ones as exemplified for the compound (III).

Suitable salts of the compound (VII) can be referred to the ones as exemplified for the compound (I).

This reaction can be carried out in substantially the same manner as Process 1, and therefore the reaction mode and reaction conditions [e.g. reactive derivatives, solvents, reaction temperature, etc.] of this reaction are to be referred to those as explained in Process 1.

[Step 2]

The compound (III) or a salt thereof can be prepared by subjecting the compound (VII) or a salt thereof to a removal reaction of the amino-protective group of $R^{10}$ in a conventional manner such as those explained in Process 2.

Method 2

[Step 1]

The compound (IX) or a salt thereof can be prepared by acylating the amino group or its reactive derivative of the compound (VIII) or a salt thereof.

Suitable salts of the compounds (VIII) and (IX) may be the same as those for the compound (I).

Suitable acylating agent used in this reaction may be a conventional acylating agent which is capable of introducing the acyl group as mentioned before such as carboxylic acid, carbonic acid, sulfonic acid and their reactive derivatives, for example, an acid halide, an acid anhydride, an activated amide, an activated ester, and the like. Preferable example of such reactive derivative may include acid chloride, acid bromide, a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.), a symmetrical acid anhydride, an activated acid amide with a heterocyclic compound containing imino function such as imidazole, 4-substituted imidazole, dimethylpyrazole, triazole and tetrazole, an activated ester (e.g. p-nitrophenyl ester, 2,4-dinitrophenyl eater, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

This reaction can be carried out in the presence of an organic or inorganic base such as alkali metal (e.g. lithium, sodium potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, 4-dimethylaminopyridine, etc.), quinoline, and the like.

In case that the acylating agent is used in a free form or its salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichioride, etc.), thionyl chloride, oxalyl chloride, N-ethylbenzisoxazolium salt, N-ethyl-5-phenylisoxazolium-3-sulfonate, a reagent (referred to as a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dichloromethane, alcohol (e.g. methanol, ethanol, etc.), tetrahydrofuran, pyridine, N,N-dimethylformamide, etc., or a mixture thereof.

The reaction temperature is not critical and the reaction is usually carried out under from cooling to heating.

[Step 2]

The object compound (II) or a salt thereof can be prepared by subjecting the compound (IX) or a salt thereof to a removal reaction of the carboxy-protective group in $R^{11}$.

This removal reaction can be carried out by a conventional method in the peptide chemistry such as solvolysis, reduction, and the like, the details of which can be referred to those of Process 2.

It is to be noted that the compound (I) and the other compounds may include one or more stereoisomers due to asymmetric carbon atoms, and all of such isomers and mixture thereof are included within the scope of this invention.

The object compound (I) and a pharmaceutically acceptable salt thereof have pharmacological activities such as endothelin antagonistic activity, particularly $ET_B$ antagonistic activity, for example, relaxating activity of blood vessel, and the like, and useful for therapeutical treatment and prevention of endothelin mediated diseases such as hypertension (e.g. essential hypertension, pulmonary hypertension, renal hypertension, etc.), heart disease such as angina pectoris, cardiomyopathy, vasospastic angina, myocardial infarction, heart failure, or the like, cerebral stroke such as cerebral arterial spasm, cerebral ischemia, cerebral infarction, cerebral embolus, cerebrovascular twitch, cerebral hemorrhage, or the like, late phase cerebral spasm after subarachnoid hemorrhage, asthma such as bronchial asthma, or the like, renal failure such acute or chronic renal failure, renal insufficiency caused by pharmaceutical (e.g. Cisplatin, Cyclosporins, FK506, etc.), peripheral circulatory failure such as Takayushi's disease, Raynaud'd disease, Buerger's disease, etc., arteriosclerosis, diabetic angiopathy such as diabetic nephropathy, diabetic retinopathy,,shock such as hemorrhagic shock, shock induced by endotoxins, etc., malignant hemangioendothelioma, organopathy after reperfusion [e.g. after organ and tissue transplantation, myocardial reperfusion injury, percutaneous transluminal coronary angiopathy (PTCA), or percutaneous transluminal coronary recanalization (PTCR), etc.], bloodstream disturbance after an operation, ulcer, irritable bowel syndrome (IBS), dysuria, retinopathy, dysmenorrhea, premature birth such as premature labor, threatened abortion, or the like, glaucoma, reocclusion after operation of PTCA, adult respiratory distress syndrome (ARDS), and the like.

For therapeutic purpose, the peptide compound (I) and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, sublingual tablet, suppositories, ointment, aerosol, infusion, ophthalmic solutions, vaginal suppository, and the like. If desired, there may be included in these preparations, auxiliary substances, stabilizing agents, wetting or emulsifying agents, buffers and other commonly used additives.

While the dosage of the compound (I) will vary depending upon the age and condition of the patient, in the case of intravenous administration, a daily dose of 0.01–100 mg of the active ingredient per kg weight of human being, in the case of intramuscular administration, a daily dose of 0.05–100 mg of the same per kg weight of human being, in case of oral administration, a daily dose of 0.1–100 mg of the same per kg weight of human being is generally given for the treatment of endothelin-mediated diseases.

In order to illustrate the usefulness of the object compound (I), the pharmacological test data of a representative compound of the compound (I) are shown in the following.

Test 1

Radioligand binding assay:

(1) Test Compound

Compound A [The compound of Example 13-6)]

(2) Test Method (a) Crude receptor membrane preparation:

Membranes as endothelin receptors were isolated from inner medulla of porcine kidney. The inner medulla of porcine kidney was placed in ice-cold buffer (0.25M sucrose, 5 mM Tris-HCl, 0.1 mM EDTA, pH 7.5). The inner medulla was homogenized in five volumes (w/v) of ice-cold buffer using a Brinkman Polytron PT-10 at a setting of 16,000 rpm for three 10-sec periods. The homogenate was centrifuged at 10,000×g for 20 minutes at 4° C. The pellet was discarded and the supernatant was centrifuged at 100,000×g for 60 minutes at 4° C. The final pellet was resuspended in three volumes of original wet weight of 50 mM Tris-HCl, pH 7.5 buffer (buffer 1) containing 100 mM NaCl, 5 mM $MgCl_2$, 1.5 µg/ml of (p-amidinophenyl)-methanesulfonyl fluoride, 120 µg/ml of bacitracin, 12 µg/ml of leupeptin, 6 µg/ml of chymostatin and 10 µg/ml of phosphoramidon for use in the assay.

(b) $^{125}$I-endothelin(ET)-1 binding assay:

To determine [$^{125}$I]ET-1 binding to kidney, membrane suspensions prepared from kidney (10 µg of protein) were incubated by constant shaking for 60 minutes at 23° C. with [$^{125}$I]ET-1 (range, 4–900 pM) in a total volume of 250 µl of buffer 1 that contained 0.1 mg/ml of bovine serum albumin. In this study, a wide range of [$^{125}$I]ET-1 concentrations was used in order to ascertain that [$^{125}$I]ET-1 has a single class of binding sites in each preparation. The incubation, which was performed in duplicate, was terminated by rapid filtration through a Whatman GF/C glass filter disk. The filter disks were washed three times with 0.2 ml of ice-cold 50 mM Tris-HCl buffer (pH 7.5), and the radioactivity was counted in a gamma counter (Hewlett-Packard) with an efficiency of 71%. Nonspecific binding was defined as nondisplaceable binding of 3.2 µMET-1, and specific binding was defined as the difference between total and nonspecific binding. The $K_d$ was determined by Scatchard analysis.

For determination of inhibition curves of test compounds, the membrane suspensions prepared from inner medulla of porcine kidney were incubated with increasing concentrations of test compounds and [$^{125}$I]ET-1 (16 pM). Specific binding represented 85% of total binding with 16 pM [$^{125}$I]ET-1 in porcine kidney. Protein concentration was determined by the dye-binding assay method (Bio-Rad protein assay kit). The $K_i$ for interaction of each compound with the binding sites was calculated from the equation of Williams et al. (J. Biol. Chem. 251, 6915–6923, 1976).

(3) Test Result
The result is shown in Table 1.

TABLE 1

| Effect on specific binding of [$^{125}$I]ET-1 in porcine kidney membrane | |
|---|---|
| Test compound | IC$_{50}$ (M) |
| A | 6.8 × 10$^{-8}$ |

From the results of the above-mentioned biological test, it is clear that compound (I) has endothelin antagonistic activity, therefore are useful for the treatment and prevention of endothelin mediated diseases, for example, hypertension, heart disease such as angina pectoris, cardiomyopathy, myocardial infarction or the like, organopathy after reperfusion [e.g. after organ and tissue plantation, myocardial reperfusion injury, PTCA, PTCR, etc.], cerebral stroke such as cerebral arterial spasm, cerebral ischemia, cerebrovascular twitch or the like, late phase cerebral spasm after subarachnoid hemorrhage, asthma such as bronchial asthma, or the like, renal failure such as chronic or acute renal failure, renal insufficiency caused by pharmaceuticals (e.g. Cisplatin, Cyclosporins, etc.), or the like.

The following examples are given for purpose of illustrating the present invention in detail.

In this specification, there are employed the following abbreviations in addition to the abbreviations adopted by the IUPAC-IUB.

| | |
|---|---|
| Boc$_2$O | di-tert-butyl dicarbonate |
| AcOH | acetic acid |
| NaOH | sodium hydroxide |
| CHCl$_3$ | chloroform |
| EDTA | ethylene diamine tetraacetate acid |
| NaCl | sodium chloride |
| DMF | dimethylformamide |
| MgCl$_2$ | magnesium chloride |
| DMSO | dimethyl sulfoxide |
| Et | ethyl |
| HOBT | N-hydroxybenzotriazole |
| Me | methyl |
| WSCD | N-ethyl-N'-(3-dimethylaminopropyl)-carbodiimide |
| EtOAc | ethyl acetate |
| HCl | hydrogen chloride |
| aq. HCl | hydrochloric acid |
| MgSO$_4$ | magnesium sulfate |
| Et$_2$O | diethyl ether |
| CH$_2$Cl$_2$ | dichloromethane |
| ET$_3$N | trimethylamine |
| MeOH | methanol |
| NaBH$_3$CN | sodium cyanoboro hydride |
| NaHCO$_3$ | sodium hydrogen carbonate |
| SiO$_2$ | silica gel |

The following Preparations and Examples are given for the purpose of illustrating the present invention in more detail.

PREPARATION 1

To a solution of N-tert-butoxycarbonyl-D-1-Nal-OH (10.0 g), HCl.H-D-Val-OMe (5.57 g) and HOBt (4.71 g) in DMF (100 ml) was added WSCD (5.41 g) at 0° C. After being stirred at room temperature for one hour, the mixture was diluted with EtOAc (500 ml) and washed with 1N aq. HCl (500 ml), water (500 ml), saturated sodium bicarbonate solution (500 ml), water (500 ml) and brine (500 ml), successively. The organic layer was dried over anhydrous MgSO$_4$ and concentrated in vacuo. The residue was dissolved in 4N aq. HCl-EtOAc (300 ml) at 0° C. After being stirred at room temperature for fifteen minutes, the mixture was concentrated in vacuo. The residue was triturated with Et$_2$O to give HCl.H-D-1-Nal-D-Val-OMe (10.0 g) as a powder.

Rf: 0.50 (10% MeOH in CHCl$_3$)

PREPARATION 2

To a stirring solution of DMSO (1.34 g) in CH$_2$Cl$_2$ (10 ml) was added dropwise a solution of oxalyl chloride (1.45 g) in CH$_2$Cl$_2$ (5 ml) at −60° C. under nitrogen atmosphere. After five minutes, a solution of N-(tert-butoxycarbonyl)-N-methylethanolamine (1.00 g) in CH$_2$Cl$_2$ (5 ml) was added dropwise to the solution and the mixture was stirred at the same temperature for five minutes. To this solution was added Et$_3$N (2.89 g) and the temperature was allowed to rise to 0° C. and the mixture was stirred at the same temperature for thirty minutes. After evaporation of the solvent, the residue was dissolved in EtOAc (50 ml) and washed with 1N aq. HCl (50 ml), water (50 ml), saturated sodium bicarbonate solution (50 ml) and brine (50 ml), successively. The organic layer was dried over anhydrous MgSO$_4$ and concentrated in vacuo to give N-(tert-butoxycarbonyl)-N-methylaminoacetaldehyde (0.74 g) as an oil.

Rf: 0.60 (EtOAc:hexane=1:1, v/v)

PREPARATION 3

To a solution of N-(tert-butoxycarbonyl)-N-methylaminoacetaldehyde (0.74 g) and HCl.H-L-Leu-OEt (836 mg) in MeOH (20 ml) was added NaBH$_3$CN (322 mg) at room temperature. After being stirred at the same temperature for thirty minutes, the solvent was evaporated in vacuo. The residue was dissolved in EtOAc (50 ml) and washed with saturated sodium bicarbonate solution (50 ml), water (50 ml) and brine (50 ml), successively. The organic layer was dried over anhydrous MgSO$_4$ and concentrated in vacuo. The residue was purified by silica gel column chromatography (SiO$_2$: 40 g, EtOAc:hexane=1:3 as an eluent) to give N-[2-[N-(tert-butoxycarbonyl)-N-methylamino]ethyl]-L-Leu-OEt (0.52 g) as an oil.

Rf: 0.57 (EtOAc:hexane=1:1, v/v)

PREPARATION 4

To a solution of (2-chlorophenyl)acetic acid (0.34 g), N-[2-[N-(tert-butoxycarbonyl)-N-methylamino]ethyl]-L-Leu-OEt (0.52 g) and HOBt (0.27 g) in DMF (8 ml) was added WSCD (0.36 g) at room temperature. After being stirred at the same temperature for eight hours, the mixture was diluted with EtOAc (40 ml) and washed with 1N aq. HCl (40 ml), water (40 ml), saturated sodium bicarbonate solution (40 ml), water (40 ml) and brine (40 ml), successively. The organic layer was dried over anhydrous MgSO$_4$ and concentrated in vacuo to give N-[2-[N-(tert-butoxycarbonyl)-N-methylamino]ethyl]-N-[(2-chlorophenyl)acetyl]-L-Leu-OEt (0.76 g) as an oil.

Rf: 0.68 (EtOAc:hexane=1:1)

PREPARATION 5

To a solution of N-[2-[N-(tert-butoxycarbonyl)-N-methylamino]ethyl]-N-[(2-chlorophenyl)acetyl]-L-Leu-OEt (0.84 g) in EtOH (12 ml) was added 1N ag. NaOH (6 ml) at room temperature. After being stirred at the same temperature for one hour, the mixture was neutralized with 1N aq. HCl (6 ml) and concentrated in vacuo. The residue was dissolved in EtOAc (40 ml) and washed with brine (40 ml).

The organic layer was dried over anhydrous MgSO$_4$ and concentrated in vacuo to give N-[2-[N-(tert-butoxycarbonyl)-N-methylamino]ethyl]-N-[(2-chlorophenyl)acetyl]-L-Leu-OH (0.75 g) as an amorphous power.

Rf: 0.34 (10% MeOH in CHCl$_3$)

PREPARATION 6

N-(tert-Butoxycarbonyl)aminoacetaldehyde (7.82 g) was obtained in substantially the same manner as that of Preparation 2.

Rf: 0.58 (EtOAc:hexane=1,1, v/v)

PREPARATION 7

N-[2-[N-(tert-Butoxycarbonyl)amino]ethyl]-L-Leu-OEt (2.60 g) was obtained in substantially the same manner as that of Preparation 3.

Rf: 0.55 (EtOAc:hexane=1:1, v/v)

PREPARATION 8

N-[2-[N-(tert-Butoxycarbonyl)amino]ethyl]-N-[(2-chlorophenyl)acetyl]-L-Leu-OEt (3.70 g) was obtained in substantially the same manner as that of Preparation 4.

Rf: 0.61 (EtOAc:hexane=1:1, v/v)

PREPARATION 9

N-[2-[N-(tert-Butoxycarbonyl)amino]ethyl]-N-[(2-chlorophenyl)acetyl]-L-Leu-OH (2.83 g) was obtained in substantially the same manner as that of Preparation 5.

Rf: 0.59 (CHCl$_3$:MeOH:AcOH=8:1:1, v/v)

PREPARATION 10

To a solution of N-tert-butoxycarbonyl-β-Ala-OH (10.0 g), N,O-dimethylhydroxylamine hydrochloride (5.67 g) and HOBt (7.86 g) in DMF (100 ml) was added WSCD (9.03 g) at 0° C. After being stirred at room temperature for four hours, the mixture was diluted with EtOAc (500 ml) and washed with 1N aq. HCl (500 ml), water (500 ml), aqueous sodium bicarbonate solution (500 ml) and brine (500 ml), successively. The organic layer was dried over anhydrous MgSO$_4$ and concentrated in vacuo to give N-tert-butoxycarbonyl-β-Ala-N,O-dimethylhydroxylamide (7.23 g) as an oil.

Rf: 0.65 (CHCl$_3$:MeOH:AcOH=16:1:1, v/v)

PREPARATION 11

To a solution of N-tert-butoxycarbonyl-β-Ala-N,O-dimethylhydroxylamide (6.20 g) in dry ethyl ether (100 ml) was added portionwise lithium aluminum hydride (1.27 g) at 0° C. After being stirred at the same temperature for twenty minutes, aqueous tartaric acid (100 ml) was added carefully and the mixture was washed with water (100 ml) and brine (100 ml), successively. The organic layer was dried over anhydrous MgSO$_4$. To this solution was added MeOH (100 ml) and HCl.H-L-Leu-OEt (5.2 g) and ethyl ether was removed under reduced pressure. NaBH$_3$CN (2.0 g) was added to the solution and the mixture was stirred at room temperature for two hours. The solvent was removed under reduced pressure and the residue was dissolved in EtOAc (100 ml) and washed with aqueous hydrogen bicarbonate solution (100 ml×2) and brine (100 ml), successively. The organic layer was dried over anhydrous MgSO$_4$ and concentrated in vacuo. The residue was purified by silica gel column chromatography (EtOAc:hexane=1:3, as an eluent) to give N-[3-(N-tert-butoxycarbonylamino)propylamino]-L-Leu-OEt (3.49 g).

Rf: 0.41 (EtOAc:hexane=1:1, v/v)

PREPARATION 12

N-[(2-Chlorophenyl)acetyl]-N-[3-[N-(tert-butoxycarbonyl)amino]propyl]-L-Leu-OEt (0.70 g) was obtained in substantially the same manner as that of Preparation 4.

Rf: 0.58 (EtOAc:hexane=1:1, v/v)

PREPARATION 13

N-[(2-Chlorophenyl)acetyl]-N-[3-[N-(tert-butoxycarbonyl)amino]propyl]-L-Leu-OH (0.56 g) was obtained in substantially the same manner as that of Preparation 5.

Rf: 0.21 (10% MeOH in CHCl$_3$)

PREPARATION 14-1)

Oxalyl chloride (38 ml) and a few drops of N,N-dimethylformamide was added to a solution of (2-chlorophenyl)acetic acid (50 g) in CH$_2$Cl$_2$ (300 ml). The mixture was stirred at room temperature for 3 hours, and then concentrated under reduced pressure. The residue was distilled under reduced pressure to give (2-chlorophenyl)acetyl chloride (41.24 g) as an oil.

bp.: 117°–118° C. (12 mm Hg)

PREPARATION 14-2)

To a solution of N-[(S)-2-(tert-butoxycarbonylamino)propyl]-L-Leu-OEt (350 mg) in CH$_2$Cl$_2$ (5 ml) was added (2-chlorophenyl)acetyl chloride (210 mg) and Et$_3$N (112 mg) at room temperature. After stirring at the same temperature for 20 minutes, the mixture was concentrated under reduced pressure. The residue was dissolved in EtOAc (15 ml) and washed with 1N aq. HCl, saturated aqueous NaHCO$_3$, and brine successively. The solution was dried over MgSO$_4$ and evaporated in vacuo. The residue was purified with SiO$_2$ column chromatography (eluted with EtOAc/n-hexane=1/3) to give N-[(S)-2-(tert-butoxycarbonylamino)propyl]-N-[(2-chlorophenyl)acetyl]-L-Leu-OEt (255 mg) as an amorphous powder.

PREPARATION 15

To a solution of N-cyclohexylglycine (0.763 g) in 1N aq. NaOH (4.86 ml) and dioxane (2 ml) was added a solution of Boc$_2$O (1.94 g) in dioxane (5 ml). The mixture was stirred at room temperature for overnight. Then 3-(N,N-dimethylamino)propylamine (0.46 g) was added to the reaction mixture. After stirring for 20 minutes, the mixture was concentrated under reduced pressure. The residue was dissolved in AcOEt (50 ml) and washed with 3.6% aq. HCl, water, and brine successively. The organic layer was dried over MgSO$_4$ and evaporated in vacuo to give N-tert-butoxycarbonyl-N-cyclohexylglycine (663.8 mg) as a white crystal.

Rf: 0.33 (10% MeOH in CHCl$_3$)

mp: 101°–103° C.

PREPARATION 16-1)

To a suspension of sodium hydride (0.4 g) in DMF (8 ml) was added dropwise a solution of 3-pyridinemethanol (1.09 g) in DMF (5 ml), and the mixture was stirred at room temperature for 30 minutes. Then a solution of tert-butyl bromoacetate (1.62 ml) in DMF (5 ml) was added to the mixture. After stirring for one hour, the reaction mixture was concentrated under reduced pressure. The residue was dissolved in AcOEt (20 ml), washed with brine, dried over MgSO$_4$, and concentrated under reduced pressure. The residue was purified with SiO$_2$ column chromatography (eluted with 1% MeOH in CHCl$_3$) to give tert-butyl (3-pyridylmethoxy)acetate (435 mg) as an oil.

Rf: 0.50 (10% MeOH in CHCl$_3$)

PREPARATION 16-2

Trifluoroacetic acid (5 ml) was added to tert-butyl (3-pyridylmethoxy)acetate (420 mg) at 0° C. After stirring at the same temperature for 40 minutes and at room temperature for 30 minutes, the reaction mixture was concentrated under reduced pressure. The residue was dissolved in 4N aq. HCl/AcOEt (4 ml) and was concentrated under reduced pressure to give (3-pyridylmethoxy)acetic acid hydrochloride (344 mg) as an amorphous powder.

Rf: 0.25 (CHCl$_3$:MeOH:AcOH=8:2:1, v/v)

PREPARATION 17-1

2-Chlorophenyl isocyanate (234 mg) was added to a solution of N-[2-(tert-butoxycarbonylamino]ethyl]-L-Leu-OEt (0.46 g) in AcOEt (10 ml). After stirring at room temperature for 10 minutes, the solution was washed with 3.5% aq. HCl saturated aqueous NaHCO$_3$ and brine successively. After drying over MgSO$_4$, the solution was evaporated under reduced pressure to give N-[2-(tert-butoxycarbonylamino)-ethyl]-N-(2-chlorophenylaminocarbonyl)-L-Leu-OEt (599 mg) as an viscous oil.

Rf: 0.66 (CHCl$_3$/AcOEt=5/1, v/v)

PROCESS 17-2

N-[2-(tert-Butoxycarbonylamino)ethyl]-N-(2-chlorophenylaminocarbonyl)-L-Leu-OH (307 mg) was obtained in substantially the same manner as that of Preparation 5.

Rf: 0.54 (benzene:AcOEt:AcOH=20:20:1, v/v)

mp: 113°–114° C.

PREPARATION 18

N-tert-Butoxycarbonyl-D-Ala-N,O-dimethylhydroxylamide (3.43 g) was obtained from N-tert-butoxycarbonyl-D-Ala-OH (3 g) and N,O-dimethylhydroxylamine hydrochloride (1.86 g), in substantially the same manner as that of Example 1.

Rf: 0.29 (EtOAc:hexane=1:1, v/v)

mp: 149° C.

PREPARATION 19-1

N-tert-Butoxycarbonyl-L-Ala-N,O-dimethylhydroxylamide (3.41 g) was obtained in substantially the same manner as that of Preparation 18.

Rf: 0.29 (EtOAc:hexane=1:1, v/v)

mp: 149° C.

PREPARATION 19-2

N-[(S)-2-(tert-Butoxycarbonylamino)propyl]-L-Leu-OEt (366 mg) was obtained in substantially the same manner as that of Preparation 11.

Rf: 0.53 (EtOAc:hexane=1:1, v/v)

PREPARATION 20

N-[(S)-2-(tert-Butoxycarbonylamino)propyl]-L-[(2-chlorophenyl)acetyl]-L-Leu-OH (323 mg) was obtained in substantially the same manner as that of Preparation 5.

Rf: 0.42 (10% MeOH in CHCl$_3$)

PREPARATION 21

N-cyclohexylglycine (0.76 g) was obtained from cyclohexanone (0.5 g) and glycine (0.654 g) in substantially the same manner as that of Preparation 3.

Rf: 0.53 (n-BuOH:AcOH:H$_2$O=5:2:3, v/v)

mp: 189°–190° C.

PREPARATION 22

N-t-Butoxycarbonyl-N-cyclohexylglycine N,O-dimethylhydroxylamide (232 mg) was obtained in substantially the same manner as that of Preparation 18.

Rf: 0.38 (AcOEt:n-hexane=1:1, v/v)

mp: 67°–68° C.

PREPARATION 23

N-Methyl-N-methoxy-2-(3-pyridylmethoxy)acetamide (206 mg) was obtained in substantially the same manner as that of Preparation 18.

Rf: 0.32 (10% MeOH in CHCl$_3$)

PREPARATION 24-1

Boc-L-Leu-D-1-Nal-D-Val-OMe (1.44 g) was obtained from Boc-L-Leu-OH (0.82 g) and D-1-Nal-D-Val-OMe.HCl (1.19 g) in substantially the same manner as that of Example 1.

Rf: 0.51 (AcOEt:n-hexane=1:1, v/v)

mp: 173°–174° C.

PREPARATION 24-2

L-Leu-D-1-Nal-D-Val-OMe.HCl (1.46 g) was obtained in substantially the same manner as that of Example 2.

Rf: 0.45 (10% MeOH in CHCl$_3$)

PREPARATION 25

N-[2-(3-Pyridylmethoxy)ethyl]-L-Leu-D-1-Nal-D-Val-OMe (259.5 mg) was obtained from N-methyl-N-methoxy-2-(3-pyridylmethoxy)acetamide (176 mg) and L-Leu-D-1-Nal-D-Val-OMe.HCl (200 mg) in substantially the same manner as that of Preparation 11.

Rf: 0.49 (10% MeOH in CHCl$_3$)

PREPARATION 26-1

Boc-D-1-Nal-D-Cys(Me)-OMe (92 mg) was obtained in substantially the same manner as that of the former part of Preparation 1.

Rf: 0.63 (CHCl$_3$:MeOH:AcOH=16:1:1, v/v)

mp: 127°–129° C.

PREPARATION 26-2

D-1-Nal-D-Cys(Me)-OMe.HCl (70 mg) was obtained in substantially the same manner as that of the latter part of Example 2.

Rf: 0.16 (CHCl$_3$:MeOH:AcOH=16:1:1, v/v)

mp: 211°–213° C. (decomp.)

PREPARATION 27

HCl.(4S)-4-[(H-D-1-Nal)amino]-6-methylheptanoic acid ethyl ester (0.35 g) was obtained in substantially the same manner as that of Preparation 1.

Rf: 0.59 (10% MeOH in CHCl$_3$)

PREPARATION 28

HCl.H-D-Trp(Me)-D-Val-OMe (3.54 g) was obtained in substantially the same manner as that of Preparation 1.

Rf: 0.48 (10% MeOH in CHCl$_3$)

PREPARATION 29

HCl.H-β-(3-benzo[b]thienyl)-D-Ala-D-Val-OMe (3.65 g) was obtained in substantially the same manner as that of Preparation 1.

Rf: 0.50 (10% MeOH in CHCl$_3$)

PREPARATION 30

N-[2-(N-t-Butoxycarbonyl-N-cyclohexylamino)ethyl]-L-Leu-D-1-Nal-D-Val-OMe (71.7 mg) was obtained in substantially the same manner as that of Preparation 25.

Rf: 0.30 (AcOEt:n-hexane=1:1, v/v)

EXAMPLE 1

To a solution of N-[2-[N-(tert-butoxycarbonyl)-N-methylamino]ethyl]-N-[(2-chlorophenyl)acetyl]-L-Leu-OH (0.74 g), HCl.H-D-1-Nal-D-Val-OMe (0.61 g) and HOBt (0.27 g) in DMF (13 ml) was added WSCD (0.31 g) at 0° C. After being stirred at room temperature for one hour, the mixture was diluted with EtOAc (70 ml) and washed with 1N aq. HCl (70 ml), water (70 ml), saturated sodium bicarbonate solution (70 ml), water (70 ml) and brine (70 ml), successively. The organic layer was dried over anhydrous MgSO$_4$ and concentrated in vacuo to give N-[2-[N-(tert-butoxycarbonyl)-N-methylamino]ethyl]-N-[(2-chlorophenyl)acetyl]-L-Leu-D-1-Nal-D-Val-OMe (1,18 g) as an amorphous powder.

Rf: 0.75 (10% MeOH in CHCl$_3$)

EXAMPLE 2

A solution of N-[2-[N-(tert-butoxycarbonyl)-N-methylamino]ethyl]-N-[(2-chlorophenyl)acetyl]-L-Leu-D-1-Nal-D-Val-OMe (1.17 g) in 4N aq. HCl-EtOAc (30 ml) was stirred at room temperature for thirty minutes. The mixture was concentrated in vacuo and the residue was triturated with Et$_2$O to give N-[(2-chlorophenyl)acetyl]-N-[2-(N-methylamino)ethyl]-L-Leu-D-1-Nal-D-Val-OMe.HCl (0.94 g) as a powder.

Rf: 0.38 (10% MeOH in CHCl$_3$)

EXAMPLE 3

N-(2-Chlorophenylacetyl)-N-[2-(N-methylamino)ethyl]-L-Leu-D- 1-Nal-D-Val-OH (0.18 g) was obtained in substantially the same manner as that of Example 13-1).

Rf: 0.27 (CHCl$_3$:MeOH:AcOH=8:1:1, v/v)
mp: 125°–129° C.

EXAMPLE 4

N-[2-[N-(tert-Butoxycarbonyl)amino]ethyl]-N-[(2-chlorophenyl)acetyl]-L-Leu-D-1-Nal-D-Val-OMe (4.31 g) was obtained in substantially the same manner as that of Example 1.

Rf: 0.73 (10% MeOH in CHCl$_3$)

EXAMPLE 5

N-(2-Aminoethyl)-N-[(2-chlorophenyl)acetyl]-L-Leu-D-1-Nal-D-Val-OMe.HCl (3.19 g) was obtained in substantially the same manner as that of Example 2.

Rf: 0.35 (10% MeOH in CHCl$_3$)

EXAMPLE 6

N-[2-(N-Benzylamino)-ethyl]-N-[(2-chlorophenyl)acetyl]-L-Leu-D-1-Nal-D-Val-OMe (0.68 g) was obtained in substantially the same manner as that of Example 12-1).

Rf: 0.54 (10% MeOH in CHCl$_3$)

EXAMPLE 7

N-[2-(N-Benzylamino)ethyl]-N-[(2-chlorophenyl)acetyl]-L-Leu-D-1-Nal-D-Val-OH (0.15 g) was obtained in substantially the same manner as that of Example 13-1).

Rf: 0.35 (10% MeOH in CHCl$_3$)
mp: 125°–132° C.

EXAMPLE 8

N-[(2-Chlorophenyl)acetyl]-N-[2-(N,N-dibenzylamino)ethyl]-L-Leu-D-1-Nal-D-Val-OMe (0.24 g) was obtained from N-(2-aminoethyl)-N-[(2-chlorophenyl)acetyl]-L-Leu-D-1-Nal-D-Val-OMe.HCl (1.00 g) in substantially the same manner as that of Example 12-1).

Rf: 0.83 (10% MeOH in CHCl$_3$)

EXAMPLE 9

N-[(2-Chlorophenyl)acetyl]-N-[2-(N,N-dibenzylamino)ethyl]-L-Leu-D-1-Nal-D-Val-OH (0.19 g) was obtained in substantially the same manner as that of Example 13-1).

Rf: 0.31 (5% MeOH in CHCl$_3$)
mp: 114°–122° C.

EXAMPLE 10

N-[2-(N-Benzyl-N-n-butylamino)ethyl]-N-[(2-chlorophenyl)acetyl]-L-Leu-D-1-Nal-D-Val-OMe (0.18 g) was obtained from N-[2-(N-benzylamino)ethyl]-N-[(2-chlorophenyl)acetyl]-L-Leu-D-1-Nal-D-Val-OMe (0.20 g) in substantially the same manner as that of Example 12-1).

Rf: 0.94 (10% MeOH in CHCl$_3$)

EXAMPLE 11

N-[2-(N-Benzyl-N-n-butylamino)ethyl]-N-[(2-chlorophenyl)acetyl]-L-Leu-D-1-Nal-D-Val-OH (0.13 g) was obtained in substantially the same manner as that of Example 13-1).

Rf: 0.50 (10% MeOH in CHCl$_3$)
mp: 103°–109° C.

EXAMPLE 12-1)

To a solution of N-[(2-chlorophenyl)acetyl]-N-[2-(N-methylamino)ethyl]-L-Leu-D-1-Nal-D-Val-OMe.HCl (100 mg) and benzaldehyde (19 mg) in MeOH (2 ml) was added NaBH$_3$CN (18 mg) at room temperature. After being stirred at the same temperature for two hours, the mixture was concentrated in vacuo. The residue was dissolved in EtOAc (20 ml) and washed with saturated sodium bicarbonate solution (20 ml×2) and brine (20 ml), successively. The organic layer was dried over anhydrous MgSO₄ and concentrated in vacuo. The residue was purified with silica gel thin layer chromatography (5% MeOH in CHCl₃) to give N-[2-(N-benzyl-N-methylamino)ethyl]-N-[(2-chlorophenyl)acetyl]-L-Leu-D-1-Nal-D-Val-OMe (83 mg) as an oil.

Rf: 0.76 (10% MeOH in CHCl₃)

The following compounds were obtained in substantially the same manner as that of Example 12-1).

EXAMPLE 12-2)

N-[(2-Chlorophenyl)acetyl]-N-[2-(N,N-dimethylamino)ethyl]-L-Leu-D-1-Nal-D-Val-OMe (0.19 g)

Rf: 0.65 (10% MeOH in CHCl₃)

EXAMPLE 12-3)

N-[(2-Chlorophenyl)acetyl]-N-[2-[N-methyl-N-(1-naphthylmethyl)amino]ethyl]-L-Leu-D-1-Nal-D-Val-OMe (0.16 g )

Rf: 0.80 (5% MeOH in CHCl₃)

EXAMPLE 12-4)

N-[(2-Chlorophenyl)acetyl]-N-[2-[N-methyl-N-(2-naphthylmethyl)amino]ethyl]-L-Leu-D-1-Nal-D-Val-OMe (0.14 g)

Rf: 0.80 (5% MeOH in CHCl₃)

EXAMPLE 12-5)

N-[(2-Chlorophenyl)acetyl]-N-[2-[N-methyl-N-(2-pyridylmethyl)amino]ethyl]-L-Leu-D-1-Nal-D-Val-OMe (90 mg)

Rf: 0.44 (5% MeOH in CHCl₃)

EXAMPLE 12-6)

N-[(2-Chlorophenyl)acetyl]-N-[2-[N-methyl-N-(3-pyridylmethyl)amino]ethyl]-L-Leu-D-1-Nal-D-Val-OMe (0.18 g)

Rf: 0.40 (5% MeOH in CHCl₃)

EXAMPLE 12-7)

N-[(2-Chlorophenyl)acetyl]-N-[2-[N-methyl-N-(4-pyridylmethyl)amino]ethyl]-L-Leu-D-1-Nal-D-Val-OMe (0.12 g)

Rf: 0.40 (5% MeOH in CHCl₃)

EXAMPLE 12-8)

N-[2-[N-(2-Chlorobenzyl)-N-methylamino]ethyl]-N-[(2-chlorophenyl)acetyl]-L-Leu-D-1-Nal-D-Val-OMe (0.22 g)

Rf: 0.74 (10% MeOH in CHCl₃)

EXAMPLE 12-9)

N-[2-[N-(3-Chlorobenzyl)-N-methylamino]ethyl]-N-[(2-chlorophenyl)acetyl]-L-Leu-D-1-Nal-D-Val-OMe (0.22 g)

Rf: 0.74 (10% MeOH in CHCl₃)

EXAMPLE 12-10)

N-[2-[N-(4-Chlorobenzyl)-N-methylamino]ethyl]-N-[(2-chlorophenyl)acetyl]-L-Leu-D-1-Nal-D-Val-OMe (0.21 g)

Rf: 0.74 (10% MeOH in CHCl₃)

EXAMPLE 12-11)

N-[(2-Chlorophenyl)acetyl]-N-[2-[N-(2-methylbenzyl)-N-methylamino]ethyl]-L-Leu-D-1-Nal-D-Val-OMe (0.18 g)

Rf: 0.74 (10% MeOH in CHCl₃)

EXAMPLE 12-12)

N-[(2-Chlorophenyl)acetyl]-N-[2-[N-(3-methylbenzyl)-N-methylamino]ethyl]-L-Leu-D-1-Nal-D-Val-OMe (0.16 g)

Rf: 0.74 (10% MeOH in CHCl₃)

EXAMPLE 12-13)

N-[(2-Chlorophenyl)acetyl]-N-[2-[N-(4-methylbenzyl)-N-methylamino]ethyl]-L-Leu-D-1-Nal-D-Val-OMe (0.19 g)

Rf: 0.74 (10% MeOH in CHCl₃)

EXAMPLE 12-14)

N-[(2-Chlorophenyl)acetyl]-N-[2-[N-(2-methoxybenzyl)-N-methylamino]ethyl]-L-Leu-D-1-Nal-D-Val-OMe (0.17 g)

Rf: 0.74 (10% MeOH in CHCl₃)

EXAMPLE 12-15)

N-[(2-Chlorophenyl)acetyl]-N-[2-[N-(3-methoxybenzyl)-N-methylamino]ethyl]-L-Leu-D-1-Nal-D-Val-OMe (0.13 g)

Rf: 0.74 (10% MeOH in CHCl₃)

EXAMPLE 12-16)

N-[(2-Chlorophenyl)acetyl]-N-[2-[N-(4-methoxybenzyl)-N-methylamino]ethyl]-L-Leu-D-1-Nal-D-Val-OMe (0.12 g)

Rf: 0.74 (10% MeOH in CHCl₃)

EXAMPLE 13-1)

To a solution of N-[2-(N-benzyl-N-methylamino)ethyl]-N-[(2-chlorophenyl)acetyl]-L-Leu-D-1-Nal-D-Val-OMe (73 mg) in EtOH (2 ml) was added 1N aq. NaOH (1 ml) at room temperature. After being stirred at the same temperature for thirty minutes, the mixture was neutralized with 1N aq. HCl (1 ml) and concentrated in vacuo. The residue was dissolved in EtOAc (20 ml) and washed with brine (20 ml). The organic layer was dried over anhydrous MgSO₄ and concentrated in vacuo. The residue was triturated with Et₂O to give N-[2-(N-benzyl-N-methylamino)ethyl]-N-[(2-chlorophenyl)acetyl]-L-Leu-D-1-Nal-D-Val-OH (65 mg).

Rf: 0.30 (CHCl₃:MeOH:AcOH=8:1:1, v/v)

mp: 125°–132° C.

The following compounds were obtained in substantially the same manner as that of Example 13-1).

EXAMPLE 13-2)

N-[(2-Chlorophenyl)acetyl]-N-[2-(N,N-dimethylamino)ethyl]-L-Leu-D-1-Nal-D-Val-OH (135 mg)

Rf: 0.19 (CHCl₃:MeOH:AcOH=16:1:1, v/v)

mp: 85°–105° C.

EXAMPLE 13-3)

N-[(2-Chlorophenyl)acetyl]-N-[2-[N-methyl-N-(1-naphthylmethyl)amino]ethyl]-L-Leu-D-1-Nal-D-Val-OH (0.12 g)

Rf: 0.40 (10% MeOH in CHCl₃)

mp: 112°–120° C.

EXAMPLE 13-4)

N-[(2-Chlorophenyl)acetyl]-N-[2-[N-methyl-N-(2-naphthylmethyl)amino]ethyl]-L-Leu-D-1-Nal-D-Val-OH (0.11 g)

Rf: 0.40 (10% MeOH in CHCl$_3$)
mp: 118°–124° C.

EXAMPLE 13-5)

N-[(2-Chlorophenyl)acetyl]-N-[2-[N-methyl-N-(2-pyridylmethyl)amino]ethyl]-L-Leu-D-1-Nal-D-Val-OH (60 mg)

Rf: 0.50 (CHCl$_3$:MeOH:AcOH=8:1:1, v/v)
mp: 84°–94° C.

EXAMPLE 13-6)

N-[(2-Chlorophenyl)acetyl]-N-[2-[N-methyl-N-(3-pyridylmethylamino]ethyl]-L-Leu-D-1-Nal-D-Val-OH (0.13 g)

Rf: 0.48 (CHCl$_3$:MeOH:AcOH=8:1:1, v/v)
mp: 88°–96° C.

EXAMPLE 13-7)

N-[(2-Chlorophenyl)acetyl]-N-[2-[N-methyl-N-(4-pyridylmethyl)amino]ethyl]-L-Leu-D-1-Nal-D-Val-OH (95 mg)

Rf: 0.48 (CHCl$_3$:MeOH:AcOH=8:1:1, v/v)
mp: 99°–103° C.

EXAMPLE 13-8)

N-[2-[N-(2-Chlorobenzyl)-N-methylamino]ethyl]-N-[(2-chlorophenyl)acetyl]-L-Leu-D-1-Nal-D-Val-OH (0.18 g)

Rf: 0.38 (10% MeOH in CHCl$_3$)
mp: 75°–80° C.

EXAMPLE 13-9)

N-[2-[N-(3-Chlorobenzyl)-N-methylamino]ethyl]-N-[(2-chlorophenyl)acetyl]-L-Leu-D-1-Nal-D-Val-OH (0.17 g)

Rf: 0.38 (10% MeOH in CHCl$_3$)
mp: 73°–78° C.

EXAMPLE 13-10)

N-[2-[N-(4-Chlorobenzyl)-N-methylamino]ethyl]-N-[(2-chlorophenyl)acetyl]-L-Leu-D-1-Nal-D-Val-OH (0.15 g)

Rf: 0.38 (10% MeOH in CHCl$_3$)
mp: 60°–65° C.

EXAMPLE 13-11)

N-[(2-Chlorophenyl)acetyl]-N-[2-[N-(2-methylbenzyl)-N-methylamino]ethyl]-L-Leu-D-1-Nal-D-Val-OH (0.14 g)

Rf: 0.38 (10% MeOH in CHCl$_3$)
mp: 116°–127° C.

EXAMPLE 13-12)

N-[(2-Chlorophenyl)acetyl]-N-[2-[N-(3-methylbenzyl)-N-methylamino]ethyl]-L-Leu-D-1-Nal-D-Val-OH (0.12 g)

Rf: 0.38 (10% MeOH in CHCl$_3$)
mp: 113°–119° C.

EXAMPLE 13-13)

N-[(2-Chlorophenyl)acetyl]-N-[2-[N-(4-methylbenzyl)-N-methylamino]ethyl]-L-Leu-D-1-Nal-D-Val-OH (0.15 g)

Rf: 0.38 (10% MeOH in CHCl$_3$)
mp: 118°–121° C.

EXAMPLE 13-14)

N-[(2-Chlorophenyl)acetyl]-N-[2-[N-(2-methoxybenzyl)-N-methylamino]ethyl]-L-Leu-D-1-Nal-D-Val-OH (0.14 g)

Rf: 0.38 (10% MeOH in CHCl$_3$)
mp: 114°–118° C.

EXAMPLE 13-15)

N-[(2-Chlorophenyl)acetyl]-N-[2-[N-(3-methoxybenzyl)-N-methyl]amino]ethyl]-L-Leu-D-1-Nal-D-Val-OH (0.11 g)

Rf:0.38 (10% MeOH in CHCl$_3$)
mp: 98°–105° C.

EXAMPLE 13-16)

N-[(2-Chlorophenyl)acetyl]-N-[2-[N-(4-methoxybenzyl)-N-methylamino]ethyl]-L-Leu-D-1-Nal-D-Val-OH (0.10 g)

Rf: 0.38 (10% MeOH in CHCl$_3$)
mp: 110°–116° C.

EXAMPLE 14

N-[(2-Chlorophenyl)acetyl]-N-[3-[N-(tert-butoxycarbonylamino]propyl]-L-Leu-D-1-Nal-D-Val-OMe (0.90) was obtained in substantially the same manner as that of Example 1.

Rf: 0.67 (10% MeOH in CHCl$_3$)

EXAMPLE 15

N-(3-Aminopropyl)-N-[(2-chlorophenyl)acetyl]-L-Leu-D-1-Nal-D-Val-OMe.HCl (0.80 g) was obtained in substantially the same manner as that of Example 2.

Rf: 0.20 (10% MeOH in CHCl$_3$)

EXAMPLE 16

A solution of N-[(2-chlorophenyl)acetyl]-N-[2-[N-(3-pyridylmethyl)amino]ethyl]-L-Leu-D-1-Nal-D-Val-OH (0.10 g) in 4N aq. HCl-EtOAc (1 ml) was stirred at room temperature for five minutes. After evaporation of the solvent, the residue was triturated with Et$_2$O to give N-[(2-chlorophenyl)acetyl]-N-[2-[N-(3-pyridylmethyl)amino]ethyl]-L-Leu-D-1-Nal-D-Val-OH.2HCl (0.10 g).

mp: 126°–132° C.

The following compounds were obtained in substantially the same manner as that of Example 12-1).

EXAMPLE 17-1)

N-[(2-Chlorophenyl)acetyl]-N-[2-[N-(3-pyridylmethyl)amino]ethyl]-L-Leu-D-1-Nal-D-Val-OMe (0.15 g)

Rf: 0.43 (10% MeOH in CHCl$_3$)

EXAMPLE 17-2)

N-[(2-Chlorophenyl)acetyl]-N-[2-[N-(cyclohexylmethyl)amino]ethyl]-L-Leu-D-1-Nal-D-Val-OMe (0.16 g)

Rf: 0.56 (10% MeOH in CHCl$_3$)

EXAMPLE 17-3)

N-[(2-Chlorophenyl)acetyl]-N-[2-[N-(n-butyl)amino]ethyl]-L-Leu-D-1-Nal-D-Val-OMe (0.11 g)

Rf: 0.40 (10% MeOH in CHCl$_3$)

EXAMPLE 17-4)

N-[(2-Chlorophenyl)acetyl]-N-[3-[N-(3-pyridylmethyl)amino]propyl]-L-Leu-D-1-Nal-D-Val-OMe (0.14 g)

EXAMPLE 17-5)

N-[3-(N-Benzylamino)propyl]-N-[(2-chlorophenyl)acetyl]-L-Leu-D-1-Nal-D-Val-OMe (60 mg)

Rf: 0.56 (10% MeOH in CHCl$_3$)

The following compounds were obtained in substantially the same manner as that of Example 13-1).

EXAMPLE 18-1)

N-[(2-Chlorophenyl)acetyl]-N-[2-[N-(3-pyridylmethyl)amino]ethyl]-L-Leu-D-1-Nal-D-Val-OH (0.12 g)

Rf: 0.14 (10% MeOH in CHCl$_3$)

EXAMPLE 18-2)

N-[(2-Chlorophenyl)acetyl]-N-[2-[N-(cyclohexylmethyl)amino]ethyl]-L-Leu-D-1-Nal-D-Val-OH (89 mg)

Rf: 0.27 (10% MeOH in CHCl$_3$)

mp: 123°–128° C.

EXAMPLE 18-3)

N-[2-[N-(n-Butyl)amino]ethyl]-N-[(2-chlorophenyl)acetyl]-L-Leu-D-1-Nal-D-Val-OH (67 mg)

Rf: 0.27 (10% MeOH in CHCl$_3$)

mp: 100°–113° C.

EXAMPLE 18-4)

N-[(2-Chlorophenyl)acetyl]-N-[3-[N-(3-pyridylmethyl)amino]propyl]-L-Leu-D-1-Nal-D-Val-OH (95 mg)

Rf: 0.47 (CHCl$_3$:MeOH:AcOH=8:1:1, v/v)

mp: 117°–125° C.

EXAMPLE 18-5)

N-[3-(N-Benzylamino)propyl]-N-[(2-chlorophenyl)acetyl]-L-Leu-D-1-Nal-D-Val-OH (40.5 mg)

Rf: 0.30 (10% MeOH in CHCl$_3$)

mp: 111°–120° C.

EXAMPLE 19

N-[(2-Chlorophenyl)acetyl]-N-[2-[N-(3-pyridylmethyl)amino]ethyl]-L-Leu-D-1-Nal-D-Val-OH (140 mg) and 1N aq. NaOH (0.196 ml) was dissolved in water (15 ml). This aqueous solution was lyophilized to give N-[(2-chlorophenyl)acetyl]-N-[2-[N-(3-pyridylmethyl)amino]ethyl]-L-Leu-D-1-Nal-D-Val-ONa (138 mg) as a powder.

EXAMPLE 20-1)

N-[2-(tert-Butoxycarbonylamino)ethyl]-N-(2-chlorophenylaminocarbonyl)-L-Leu-D-1-Nal-D-Val-OMe (366 mg) was obtained in substantially the same manner as that of Example 1.

Rf: 0.40 (AcOEt:n-hexane=1:1, v/v)

EXAMPLE 20-2)

N-[2-(tert-Butoxycarbonylamino)ethyl]-N-(2-chlorophenylaminocarbonyl)-L-Leu-D-1-Nal-D-Val-OMe (431 mg) was dissolved in CH$_2$Cl$_2$ (5 ml) and trifluoroacetic acid (5 ml) at 0° C. After stirring at same temperature for 30 minutes, the solution was concentrated under reduced pressure. The residue was dissolved in AcOEt (20 ml) and was washed with saturated aqueous NaHCO$_3$ and brine, dried over MgSO$_4$, and evaporated in vacuo to give N-(2-aminoethyl)-N-(2-chlorophenylaminocarbonyl)-L-Leu-D-1-Nal-D-Val-OMe (397 mg) as an amorphous powder.

Rf: 0.19 (10% MeOH in CHCl$_3$)

EXAMPLE 20-3)

N-(2-Chlorophenylaminocarbonyl)-N-[2-[N-(3-pyridylmethyl)amino]ethyl]-L-Leu-D-1-Nal-D-Val-OMe (178 mg) was obtained in substantially the same manner as that of Example 6.

Rf: 0.38 (10% MeOH in CHCl$_3$)

EXAMPLE 20-4)

N-(2-Chlorophenylaminocarbonyl)-N-[2-[N-(3-pyridylmethyl)amino]ethyl]-L-Leu-D-1-Nal-D-Val-OH (113 mg) was obtained in substantially the same manner as that of Example 13-1).

Rf: 0.18 (CHCl$_3$:MeOH:AcOH=16:1:1, v/v)

EXAMPLE 21-1)

N-[2-[N-[(R)-2-(N-tert-Butoxycarbonylamino)propyl]amino]ethyl]-N-[(2-chlorophenyl)acetyl]-L-Leu-D-1-Nal-D-Val-OMe (130.5 mg) was obtained from N-tert-butoxycarbonyl-D-Ala-N,O-dimethylhydroxylamide (137 mg) and N-(2-aminoethyl)-N-[(2-chlorophenyl)acetyl]-L-Leu-D-1-Nal-D-Val-OMe.HCl (200 mg) in substantially the same manner as that of Preparation 11.

Rf: 0.53 (10% MeOH in CHCl$_3$)

EXAMPLE 21-2)

N-[2-[N-[(R)-2-Aminopropyl]amino]ethyl]-N-[(2-chlorophenyl)acetyl]-L-Leu-D-1-Nal-D-Val-OH (77.3 mg) was obtained in substantially the same manner as those of Examples 29-2) and 13-1).

Rf: 0.20 (10% MeOH in CHCl$_3$)

EXAMPLE 22-1)

N-[2-[N-[(S)-2-(N-tert-Butoxycarbonylamino)propyl]amino]ethyl]-N-[(2-chlorophenyl)acetyl]-L-Leu-D-1-Nal-D-Val-OMe (109 mg) was obtained in substantially the same manner as that of Preparation 11.

Rf: 0.47 (10% MeOH in CHCl$_3$)

EXAMPLE 22-2)

N-[2-[N-[(S)-2-Aminopropyl]amino]ethyl]-N-[(2-chlorophenyl)acetyl]-L-Leu-D-1-Nal-D-Val-OH (57.2 mg) was obtained in substantially the same manner as those of Examples 29-2) and 13-1).

Rf: 0.24 (10% MeOH in CHCl$_3$)

EXAMPLE 23-1)

N-[(S)-2-(tert-Butoxycarbonylamino)propyl]-N-[(2-chlorophenyl)acetyl]-L-Leu-D-1-Nal-D-Val-OMe (264 mg) was obtained in substantially the same manner as that of Example 1.

Rf: 0.42 (EtOAc:hexane=1:1, v/v)

EXAMPLE 23-2)

N-[(S)-2-Aminopropyl]-N-[(2-chlorophenyl)acetyl]-L-Leu-D-1-Nal-D-Val-OMe.HCl (189 mg) was obtained in substantially the same manner as that of Example 2.

Rf: 0.36 (10% MeOH in CHCl$_3$)

EXAMPLE 23-3)

N-[(2-Chlorophenyl)acetyl]-N-[(S)-2-[N-(3-pyridylmethyl)amino]propyl]-L-Leu-D-1-Nal-D-Val-OMe (76 mg) was obtained in substantially the same manner as that of Example 6.

Rf: 0.49 (10% MeOH in CHCl$_3$)

EXAMPLE 23-4)

N-[(2-Chlorophenyl)acetyl]-N-[(S)-2-[N-(3-pyridylmethyl)amino]propyl]-L-Leu-D-1-Nal-D-Val-OH.2HCl (49 mg) was obtained in substantially the same manner as those of Examples 13-1) and 16.

Rf: 0.53 (CHCl$_3$:MeOH:NH$_4$OH=65:25:4, v/v)

EXAMPLE 24-1)

N-[2-(N-t-Butoxycarbonyl-N-cyclohexylamino)ethyl]-N-[(2-chlorophenyl)acetyl]-L-Leu-D-1-Nal-D-Val-OMe (62.6 mg) was obtained from (2-chlorophenyl)acetic acid (18.8 mg) and N-[2-(N-t-butoxycarbonyl-N-cyclohexylamino)ethyl]-L-Leu-D-1-Nal-D-Val-OMe (66.7 mg) in substantially the same manner as that of Preparation 4.

Rf: 0.52 (AcOEt:n-hexane=1:1, v/v)

EXAMPLE 24-2)

N-[2-(N-t-Butoxycarbonyl-N-cyclohexylamino)ethyl]-N-[(2-chlorophenyl)acetyl]-L-Leu-D-1-Nal-D-Val-OH (45 mg) was obtained in substantially the same manner as that of Example 13-1).

Rf: 0.24 (10% MeOH in CHCl$_3$)

EXAMPLE 24-3)

N-[(2-Chlorophenyl)acetyl]-N-[2-(N-cyclohexylamino)ethyl]-L-Leu-D-1-Nal-D-Val-OH.HCl (28.1 mg) was obtained in substantially the same manner as that of Example 2.

Rf: 0.80 (CHCl$_3$:MeOH:NH$_4$OH=65:25:4, v/v)

EXAMPLE 25-1)

N-[(2-Chlorophenyl)acetyl]-N-[2-[N-(3-nicotinoyl)amino]ethyl]-L-Leu-D-1-Nal-D-Val-OMe (140.6 mg) was obtained from N-(2-aminoethyl)-N-[(2-chlorophenyl)acetyl]-L-Leu-D-1-Nal-D-Val-OMe.HCl (150 mg) and nicotinoyl chloride hydrochloride (44 mg) in substantially the same manner as that of Preparation 14-2).

Rf: 0.61 (10% MeOH in CHCl$_3$)

EXAMPLE 25-2)

N-[(2-Chlorophenyl)acetyl]-N-[2-[N-(3-nicotinoyl)amino]ethyl]-L-Leu-D-1-Nal-D-Val-OH (61.9 mg) was obtained in substantially the same manner as that of Example 13-1).

Rf: 0.53 (CHCl$_3$:MeOH:AcOH=8:1:1, v/v)

EXAMPLE 26-1)

N-[(2-Chlorophenyl)acetyl]-N-[2-(3-pyridylmethoxy)ethyl]-L-Leu-D-1-Nal-D-Val-OMe (155.6 mg) was obtained from (2-chlorophenyl)acetyl chloride (87 mg) and N-[2-(3-pyridylmethoxy)ethyl]-L-Leu-D-1-Nal-D-Val-OMe (241 mg) in substantially the same manner as that of Preparation 14-2).

Rf: 0.57 (10% MeOH in CHCl$_3$)

EXAMPLE 26-2)

N-[(2-Chlorophenyl)acetyl]-N-[2-(3-pyridylmethoxy)ethyl]-L-Leu-D-1-Nal-D-Val-OH (119 mg) was obtained in substantially the same manner as that of Example 13-1).

Rf: 0.65 (CHCl$_3$:MeOH:AcOH=8:1:1, v/v)

EXAMPLE 27-1)

N-[(2-Chlorophenyl)acetyl]-N-[3-(cyclohexylamino)propyl]-L-Leu-D-1-Nal-D-Val-OMe (28.6 mg) was obtained in substantially the same manner as that of Example 6.

Rf: 0.35 (10% MeOH in CHCl$_3$)

EXAMPLE 27-2)

N-[(2-Chlorophenyl)acetyl]-N-[3-(cyclohexylamino)propyl]-L-Leu-D-1-Nal-D-Val-OH (21 mg) was obtained in substantially the same manner as that of Example 13-1).

Rf: 0.28 (10% MeOH in CHCl$_3$)

EXAMPLE 28-1)

N-[2-(N-t-Butoxycarbonylamino)ethyl]-N-[(2-chlorophenyl)acetyl]-L-Leu-D-1-Nal-D-Cys(Me)-OMe (173 mg) was obtained in substantially the same manner as that of Example 4.

Rf: 0.36 (AcOEt:n-hexane=1:1, v/v)

EXAMPLE 28-2)

N-[(2-Aminoethyl)-N-[(2-chlorophenyl)acetyl]-L-Leu-D-1-Nal-D-Cys(Me)-OMe.HCl (156 mg) was obtained in substantially the same manner as that of Example 2.

Rf: 0.21 (10% MeOH in CHCl$_3$)

EXAMPLE 28-3)

N-[(2-Chlorophenyl)acetyl]-N-[2-[N-(3-pyridylmethyl)amino]ethyl]-L-Leu-D-1-Nal-D-Cys(Me)-OMe (119.1 mg) was obtained in substantially the same manner as that of Example 12-1).

Rf: 0.45 (10% MeOH in CHCl$_3$)

EXAMPLE 28-4)

N-[(2-Chlorophenyl)acetyl]-N-[2-[N-(3-pyridylmethyl)amino]ethyl]-L-Leu-D-1-Nal-D-Cys(Me)-OH (43.9 mg) was obtained in substantially the same manner as that of Example 13-1).

Rf: 0.56 (CHCl$_3$:MeOH:AcOH=8:1:1, v/v)

EXAMPLE 29-1)

(4S)-4-[N-[N-[(2-Chlorophenyl)acetyl]-N-[2-[N-(tert-butoxycarbonyl)amino]ethyl]-L-Leu-D-1-Nal]amino]-6-methylheptanoic acid ethyl ester (0.28 g) was obtained in substantially the same manner as that of Example 1.

Rf: 0.53 (EtOAc:hexane=1:1, v/v)

EXAMPLE 29-2)

(4S)-4-[N-[N-[(2-Chlorophenyl)acetyl]-N-(2-aminoethyl)-L-Leu-D-1-Nal]amino]-6-methylheptanoic acid ethyl ester hydrochloride (145 mg) was obtained in substantially the same manner as that of Example 2 by using TFA instead of aqueous HCl.

Rf: 0.24 (10% MeOH in CHCl$_3$)

EXAMPLE 29-4)

(4S)-4-[N-[N-[(2-Chlorophenyl)acetyl]-N-[2-[N-(3-pyridylmethyl)amino]ethyl]-L-Leu-D-1-Nal]amino]-6-methylheptanoic acid (55 mg) was obtained in substantially the same manner as that of Example 13-1).

Rf: 0.42 (CHCl₃:MeOH:AcOH=8:1:1, v/v)
mp: 85°–88° C.

EXAMPLE 29-3)

(4S)-4-[N-[N-[(2-Chlorophenyl)acetyl]-N-[2-[N-(3-pyridylmethyl)amino]ethyl]-L-Leu-D-1-Nal]amino]-6-methylheptanoic acid ethyl ester (0.12 g) was obtained in substantially the same manner as that of Example 12-1).

Rf: 0.52 (10% MeOH in CHCl₃)

EXAMPLE 30-1)

N-[(2-Chlorophenyl)acetyl]-N-[2-[N-(tert-butoxycarbonyl)amino]ethyl]-L-Leu-D-Trp(Me)-D-Val-OMe (0.20 g) was obtained in substantially the same manner as that of Example 1.

Rf: 0.46 (EtOAc:hexane=1:1, v/v)

EXAMPLE 30-2)

N-[(2-Chlorophenyl)acetyl]-N-(2-aminoethyl)-L-Leu-D-Trp(Me)-D-Val-OMe hydrochloride (135 mg) was obtained in substantially the same manner as that of Example 29-2).

Rf: 0.21 (10% MeOH in CHCl₃)

EXAMPLE 30-3)

N-[(2-Chlorophenyl)acetyl]-N-[2-[N-(3-pyridylmethyl)amino]ethyl]-L-Leu-D-Trp(Me)-D-Val-OMe (0.12 g) was obtained in substantially the same manner as that of Example 12-1).

Rf: 0.49 (10% MeOH in CHCl₃)

EXAMPLE 30-4)

N-[(2-Chlorophenyl)acetyl]-N-[2-[N-(3-pyridylmethyl)amino]ethyl]-L-Leu-D-Trp(Me)-D-Val-OH (80 mg) was obtained in substantially the same manner as that of Example 13-1).

Rf: 0.43 (CHCl₃:MeOH:AcOH=8:1:1, v/v)
mp: 115°–135° C.

EXAMPLE 31-1)

N-[(2-Chlorophenyl)acetyl]-N-[2-[N-(tert-butoxycarbonyl)amino]ethyl]-L-Leu-β-(3-benzo[b]thienyl)-D-Ala-D-Val-OMe (0.32 g) was obtained in substantially the same manner as that of Example 1.

Rf: 0.48 (EtOAc:hexane=1:1, v/v)

EXAMPLE 31-2)

N-[(2-Chlorophenyl)acetyl]-N-(2-aminoethyl)-L-Leu-β-(3-benzo[b]thienyl)-D-Ala-D-Val-OMe (156 mg) was obtained in substantially the same manner as that of Example 29-2).

Rf: 0.26 (10% MeOH in CHCl₃)

EXAMPLE 31-3)

N-[(2-Chlorophenyl)acetyl]-N-[2-[N-(3-pyridylmethyl)amino]ethyl]-L-Leu-β-(3-benzo[b]thienyl)-D-Ala-D-Val-OMe (0.15 g) as obtained in substantially the same manner as that of Example 12-1).

Rf: 0.43 (10% MeOH in CHCl₃)

EXAMPLE 31-4)

N-[(2-Chlorophenyl)acetyl]-N-[2-[N-(3-pyridylmethyl)amino]ethyl]-L-Leu-β-(3-benzo[b]thienyl)-D-Ala-D-Val-OH (103 mg) was obtained in substantially the same manner as that of Example 13-1).

Rf: 0.46 (CHCl₃:MeOH:AcOH=8:1:1, v/v)
mp: 122°–140° C.

We claim:
1. A compound of the formula:

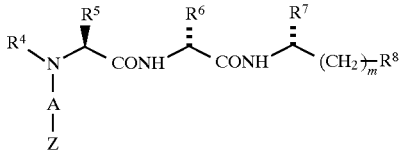

in which
R⁴ is acyl,
R⁵ is lower alkyl,
R⁶ is optionally substituted ar(lower)alkyl or optionally substituted heterocyclic-(lower)alkyl,
R⁷ is lower alkyl or lower alkylthio(lower)alkyl,
R⁸ is carboxy or protected carboxy,
A is lower alkylene,
Z is a group of the formula:

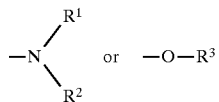

wherein
R¹ is hydrogen, lower alkyl, common amino-protective group or optionally substituted ar(lower)alkyl,
R² is hydrogen, lower alkyl, optionally substituted ar(lower)alkyl, optionally substituted heterocyclic-(lower)alkyl, optionally substituted cyclo(lower)alkyl (lower)alkyl, common amino-protective group, amino (or protected amino)(lower)alkyl, optionally substituted heterocyclic-carbonyl or cyclo(lower)alkyl, and
R³ is optionally substituted heterocyclic(lower)alkyl, and
m is an integer of 0 to 2,
or pharmaceutically acceptable salts thereof.
2. The compound of claim 1, wherein
R¹ is hydrogen, lower alkyl, lower alkoxycarbonyl, C₆–C₁₀ ar(lower)alkyl optionally substituted by the group consisting of hydroxy, protected hydroxy, halogen, lower alkyl and lower alkoxy, or naphthyl (lower)alkyl,
R² is hydrogen, lower alkyl, C₆–C₁₀ ar(lower)alkyl optionally substituted by the group consisting of hydroxy, protected hydroxy, halogen, lower alkyl and lower alkoxy, naphthyl(lower)alkyl, heterocyclic (lower)alkyl or heterocyclic-carbonyl optionally substituted by the group consisting of hydroxy, protected hydroxy, halogen, lower alkyl, lower alkoxy and imino-protective group, each of said heterocyclic group being unsaturated 5 or 6-membered heteromonocyclic group containing 1 to 4 nitrogen atom(s), cyclo(lower)alkyl (lower)alkyl optionally substituted by the group consisting of hydroxy, protected hydroxy, halogen, lower alkyl and lower alkoxy, cyclo(lower)alkyl or lower alkoxycarbonyl,
R³ is heterocyclic-(lower)alkyl optionally substituted by the group consisting of hydroxy, protected hydroxy, halogen, lower alkyl, lower alkoxy and imino-protective group, said heterocyclic group being unsaturated 5 or 6-membered heteromonocyclic group containing 1 to 4 nitrogen atom(s), $R^4$ is $C_6$–$C_{10}$ ar(lower)alkanoyl or $C_6$–$C_{10}$ arylcarbamoyl, each of which is optionally substituted by the group consisting of hydroxy, protected hydroxy, halogen, lower alkyl and lower alkoxy, $R^5$ is lower alkyl, $R^6$ is $C_6$–$C_{10}$ ar(lower)alkyl optionally substituted by the group consisting of hydroxy, protected hydroxy, halogen, lower alkyl and lower alkoxy, naphthyl(lower)alkyl, or heterocyclic(lower)alkyl optionally substituted by the group consisting of hydroxy, protected hydroxy, halogen, lower alkyl and lower alkoxy, said heterocyclic group being unsaturated 5 or 6-membered heteromonocyclic group containing 1 to 4 nitrogen atom(s), unsaturated condensed 7 to 12-membered heterocyclic group containing 1 to 5 nitrogen or unsaturated condensed 7 to 12-membered heterocyclic group containing 1 to 3 sulfur atom(s), $R^7$ is lower alkyl or lower alkylthio(lower)alkyl, $R^8$ is carboxy or esterified carboxy, A is lower alkylene, and m is an integer of 0 to 2.

3. The compound of claim 2, wherein $R^1$ is hydrogen, lower alkyl, lower alkoxycarbonyl, phenyl(lower)alkyl optionally substituted by the group consisting of halogen, lower alkyl and lower, alkoxy, or naphthyl(lower)alkyl, $R^2$ is hydrogen, lower alkyl, phenyl(lower)alkyl optionally substituted by the group consisting of halogen, lower alkyl and lower alkoxy, naphthyl(lower)alkyl, heterocyclic(lower)alkyl or heterocyclic-carbonyl, each of said heterocyclic group being pyrrolyl, pyrrolinyl, imidazolyl, pyrazolyl, pyridyl, pyridyl N-oxide, pyrimidyl, pyrazinyl, pyridazinyl, triazolyl, tetrazolyl or dihydrotriazinyl, cyclo(lower)alkyl(lower)alkyl, cyclo(lower)alkyl or lower alkoxycarbonyl, $R^3$ is heterocyclic-(lower)alkyl, said heterocyclic group being pyrrolyl, pyrrolinyl, imidazolyl, pyrazolyl, pyridyl, pyridyl N-oxide, pyrimidyl, pyrazinyl, pyridazinyl, triazolyl, tetrazolyl or dihydrotriazinyl, $R^4$ is halophenyl(lower)alkanoyl or halophenylcarbamoyl, $R^5$ is lower alkyl, $R^6$ is naphthyl(lower)alkyl, or heterocyclic(lower)alkyl optionally substituted by lower alkyl, said heterocyclic group being pyrrolyl, pyrrolinyl, imidazolyl, pyrazolyl, pyridyl, and its N-oxide, pyrimidyl, pyrazinyl, pyridazinyl, triazolyl, tetrazolyl, dihydrotriazinyl, indolyl, isoindolyl, indoliziyl, benzimidazolyl, quinolyl, isoquinolyl, indazolyl, benzotriazolyl, tetrazolopyridyl, tetrazolopyridazinyl, dihydrotriazolopyridazinyl or benzothienyl, $R^7$ is lower alkyl or lower alkylthio(lower)alkyl, $R^8$ is carboxy or lower alkoxycarbonyl, A is lower alkylene, and m is an integer of 0 to 2.

4. The compound of claim 3, wherein

A is a group of the formula:

$$-N\begin{matrix}R^1\\R^2\end{matrix}$$

in which $R^1$ is hydrogen, lower alkyl or phenyl(lower)alkyl, $R^2$ is hydrogen, lower alkyl, phenyl(lower)alkyl, halophenyl(lower)alkyl, methylphenyl(lower)alkyl, methoxyphenyl(lower)alkyl, naphthyl(lower)alkyl, pyridyl(lower)alkyl, cyclo(lower)alkyl(lower)alkyl, pyridylcarbonyl or cyclo(lower)alkyl, $R^4$ is halophenyl(lower)alkanoyl or halophenylcarbamoyl, $R^5$ is lower alkyl, $R^6$ is naphthyl(lower)alkyl, lower alkylindolyl(lower)alkyl or benzothienyl(lower)alkyl, $R^7$ is lower alkyl or lower alkylthio(lower)alkyl, $R^8$ is carboxy, A is lower alkylene, and m is an integer of 0 to 2.

5. The compound of claim 4, wherein $R^1$ is hydrogen, $C_1$–$C_4$ alkyl, $C_1$–$C_4$ alkoxycarbonyl or phenyl($C_1$–$C_4$)alkyl, $R^2$ is hydrogen, $C_1$–$C_4$ alkyl, phenyl($C_1$–$C_4$)alkyl, halophenyl($C_1$–$C_4$)alkyl, methylphenyl($C_1$–$C_4$)alkyl, methoxyphenyl($C_1$–$C_4$)alkyl, naphthyl($C_1$–$C_4$)alkyl, pyridyl($C_1$–$C_4$)alkyl, cyclo($C_1$–$C_4$)alkyl($C_1$–$C_4$)alkyl, pyridylcarbonyl, cyclo($C_1$–$C_4$)alkyl or $C_1$–$C_4$ alkoxycarbonyl, $R^4$ is halophenyl($C_1$–$C_4$)alkanoyl or halophenylcarbamoyl, $R^5$ is $C_1$–$C_4$ alkyl, $R^6$ is naphthyl($C_1$–$C_4$)alkyl, $C_1$–$C_4$ alkylindolyl($C_1$–$C_4$)alkyl or benzothienyl($C_1$–$C_4$)alkyl, $R^7$ is $C_1$–$C_4$ alkyl or $C_1$–$C_4$ alkylthio($C_1$–$C_4$)alkyl, A is $C_1$–$C_4$ alkylene, and m is an integer of 0 to 2.

6. A process for the preparation of the compound of claim 1, or salts thereof, which comprises (a) reacting a compound of the formula:

$$R^4\text{—}\underset{\underset{Z}{\overset{\overset{R^5}{|}}{A}}}{N}\text{—COOH}$$

or its reactive derivative at the carboxy group, or a salt thereof with a compound of the formula:

$$H_2N\text{—}\overset{R^6}{\underset{}{\cdot}}\text{—CONH—}\overset{R^7}{\underset{}{\cdot}}\text{—}(CH_2)_m\text{—}R^8$$

or its reactive derivative at the amino group, or a salt thereof to give a compound of the formula:

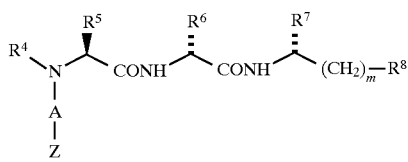

or a salt thereof; or
(b) subjecting a compound of the formula:

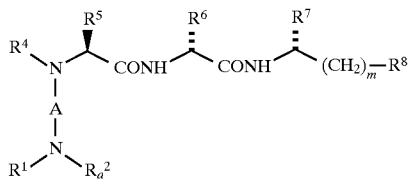

or a salt thereof to a removal reaction of the amino-protective group of $R_a^2$ to give a compound of the formula:

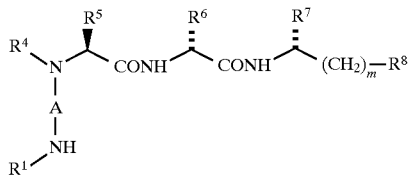

or a salt thereof; or
(c) reacting a compound of the formula:

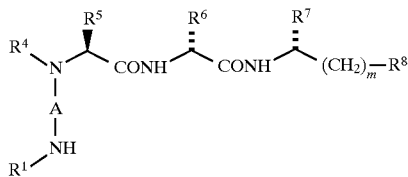

or its reactive derivative at the amino group, or a slat thereof with a compound of the formula:

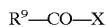

or a salt thereof in the presence of a reducing agent to give a compound of the formula:

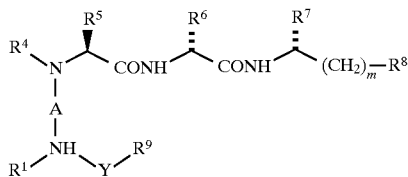

or a salt thereof; or
(d) subjecting a compound of the formula:

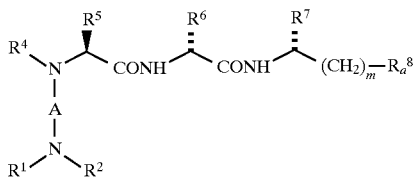

or a salt thereof to a removal reaction of the carboxy-protective group in $R_a^8$ to give a compound of the formula:

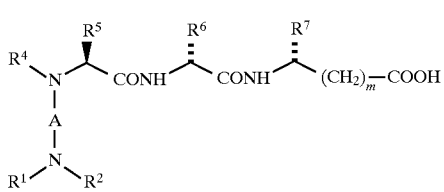

or a salt thereof;

wherein $R^1, R^2, R^3, R^4, R^5, R^6, R^7, R^8$, m and n are each as defined above, $R_a^2$ is amino-protective group, $R_a^8$ is protected carboxy, $R^9$ is hydrogen, $C_1$–$C_5$ alkyl, optionally substituted ar($C_1$–$C_5$)alkyl, optionally substituted heterocyclic ($C_1$–$C_5$)alkyl, or optionally substituted cyclo(lower)alkyl($C_1$–$C_5$)alkyl, amino(or protected amino)($C_1$–$C_5$) alkyl, X is a leaving group, and Y is methylene or carbonyl.

7. A pharmaceutical composition which comprises a compound of claim 1 or a pharmaceutically acceptable salt thereof and a pharmaceutically acceptable carrier or excipient.

8. A process for preparing a pharmaceutical composition which comprises admixing a compound of claim 1 or a pharmaceutically acceptable salt thereof with a pharmaceutically acceptable carrier or excipient.

9. A method for treating and/or preventing endothelin mediated diseases which comprises administering a compound of claim 1 or a pharmaceutically acceptable salt thereof to a human being or an animal.

* * * * *